(12) United States Patent
Su et al.

(10) Patent No.: US 9,173,383 B2
(45) Date of Patent: Nov. 3, 2015

(54) RECOMBINANT NON-HUMAN MAMMALIAN MODEL FOR HEPATITIS INFECTION AND IMMUNOPATHOGENESIS

(75) Inventors: Lishan Su, Chapel Hill, NC (US); Liguo Zhang, Chapel Hill, NC (US); Michael Washburn, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 471 days.

(21) Appl. No.: 12/918,676

(22) PCT Filed: Feb. 20, 2009

(86) PCT No.: PCT/US2009/001081
§ 371 (c)(1),
(2), (4) Date: Sep. 15, 2010

(87) PCT Pub. No.: WO2009/105244
PCT Pub. Date: Aug. 27, 2009

(65) Prior Publication Data
US 2011/0041192 A1 Feb. 17, 2011

Related U.S. Application Data

(60) Provisional application No. 61/030,328, filed on Feb. 21, 2008.

(51) Int. Cl.
*A01K 67/027* (2006.01)
*C12N 9/64* (2006.01)
*C12N 15/85* (2006.01)

(52) U.S. Cl.
CPC ......... *A01K 67/0271* (2013.01); *A01K 67/0275* (2013.01); *C12N 9/6475* (2013.01); *C12N 15/8509* (2013.01); *A01K 2207/15* (2013.01); *A01K 2217/052* (2013.01); *A01K 2217/15* (2013.01); *A01K 2217/206* (2013.01); *A01K 2217/30* (2013.01); *A01K 2227/105* (2013.01); *A01K 2267/0337* (2013.01)

(58) Field of Classification Search
CPC .............. A01K 2217/15; A01K 2227/105; A01K 2267/0337; A01K 2207/15; A01K 2217/206; A01K 2217/30; A01K 67/0271; A01K 67/0275; C07K 14/47; C07K 2319/00; C12N 15/8509; C12N 2740/16011; C12N 2740/16043
USPC .................................................. 800/8, 18, 21
See application file for complete search history.

(56) References Cited

U.S. PATENT DOCUMENTS

| | | | |
|---|---|---|---|
| 6,509,514 B1 * | 1/2003 | Kneteman et al. | 800/3 |
| 7,161,057 B2 | 1/2007 | Kneteman et al. | |
| 2005/0070014 A1 * | 3/2005 | Maruyama et al. | 435/455 |
| 2010/0325747 A1 * | 12/2010 | Grompe et al. | 800/18 |

OTHER PUBLICATIONS

Watanabe et al Blood. Jan. 1, 2007 212-218.*
Hiramatsu et al Blood, 2003, 102(3), 873-880.*
Azuma et al Nature Biotechnology, 2007, 903-910.*
Pajvani et al Nature medicine, 2005, 11, 797-803.*
Traggiai et al Science, 2004, 304, 104-107.*
Ito et al., Cellular & Molecular Immunology 9:208-214 (2012).*
Keefer Animal Reproduction Science 82-83: 5-12, 2004.*
Murray et al Theriogenology, 1999, 51:149-159.*
Bility et al Nature Protocol, 2012, 1608-1617.*
Hiramatsu H et al. Complete reconstitution of human lymphocytes from cord blood CD34+ cells using NOD/SCID/$\gamma c^{null}$ mice model. Blood. Aug. 1, 2003; 102(3): 873-880.
Traggai E et al. Development of a human adaptive immune system in cord blood cell-transplanted mice. transplanted mice. Science. Apr. 2, 2004; 304: 104-107.
Azuma H et al. Robust expansion of human hepatocytes in $Rah^{-/-}Rag2^{-/-\,Il2rg-/-}$ mice. Nature Biotechnology. Aug. 2007; 25(8): 903-910.
Schmelzer E et al. Human hepatic stem cells from fetal and postnatal donors. The Journal of Experimental Medicine. Aug. 6, 2007; 204(8): 1973-1987.
Watanabe S et al. Hematopoietic stem cell-engrafted NOD/SCID/IL2R{gamma}null mice develop human lymphoid systems and induce long-lasting HIV-1 infection with specific humoral immune responses. Blood, Jan. 1, 2007; 109(1): 212-218.
International Search Report and Written Opinion, PCT/US2009/001081, mailed Jul. 14, 2009.
Heckel JL et al. Neonatal bleeding in transgenic mice expressing urokinase-type plasminogen activator. Cell. Aug. 10, 1990; 63: 447-456.
Kubota H and Reid LM. Clonogenic hepatoblasts, common precursors for hepatocytic and biliary lineages, are lacking classical major histocompatibility complex claim I antigen. PNAS. Oct. 24, 2000; 97(22): 12132-12137.
Traggiai E et al. Development of a human adaptive immune system in cord blood cell-transplanted mice. Science. Apr. 2, 2004; 304: 104-107.
Pajvani UB et al. Fat apoptosis through targeted activation of caspase 8: a new mouse model of inducible and reversible lipoatrophy. Nature Medicine. Jul. 2005; 11(7): 797-803.
Macchiarini F et al. Humanized mice: are we there yet? JEM. Nov. 21, 2005; 202(10); 1307-1311.

(Continued)

*Primary Examiner* — Anoop Singh
(74) *Attorney, Agent, or Firm* — Myers Bigel Sibley & Sajovec, P.A.

(57) ABSTRACT

Provided herein is a recombinant non-human mammal having an immune system including human immune cells and having a liver including human liver cells, and methods for producing the same. Also provided are methods of screening a compound for activity in treating hepatitis, comprising: administering a test compound to a recombinant non-human mammal as described herein; and then detecting the presence or absence of said activity in said mammal (e.g., by biochemical assay), said presence of said activity in said mammal indicating that said compound has activity in treating hepatitis. Methods of making fusion cells useful for the production of human monoclonal antibodies are also provided.

9 Claims, 17 Drawing Sheets

(56) References Cited

OTHER PUBLICATIONS

Baenziger S et al. Disseminated and sustained HIV invection in CD34+ cord blood cell-transplanted Rag2-/-γc-/- mice. PNAS/ Oct. 24, 2006; 103(43): 15951-15956.

Azuma H et al. Robust expansion of human hepatocytes in Rah-/-/Rag2-/-/Il2rg-/- mice. Nature Biotechnology. Aug. 2007; 25(8): 903-910.

Zhang L et al. HIV-1 infection and pathogenesis in a novel humanized mouse model. Blood. Apr. 1, 2007; 109(7): 2978-2981.

Jiang Q et al. FoxP3+CD4+ regulatory T cells play an important role in acute HIV-1 infection in humanized Rag2-/-γc-/- mice in vivo. Blood. Oct. 1, 2008; 112(7): 2858-2868.

Washburn ML et al. A humanized mouse model to study hepatitis C virus infection, immune response, and liver disease. Gastroenterology. Apr. 2011; 140(4): 1334-44 Abstract.

Dolgin E. The murine candidate: small animals that mimic human hepatitis C infection will help researchers pinpoint weakness in the viral life cycle. Nature. Jun. 9, 2011; 474: S14-S15.

Washburn ML et al. A humanized mouse model to study hepatitis C virus infection, immune response, and liver disease. Gastroenterology. Apr. 2011; 140(4): 1334-1344, with Supplementary Materials Figure S1 to Figure S7.

Baas T. HCV's mighty mouse. SciBX: Science-Business eXchange. Jun. 16, 2011; 4(24): 15 pp.

Robinet E and Baumert TF. A first step towards a mouse model for hepatitis C virus infection containing a human immune system. Journal of Hepatology. 2011; 55: 718-720.

Berges BK and Rowan MR. The utility of the new generation of humanized mice to study HIV-1 infection: transmission, prevention, pathogenesis, and treatment. Retrovirology. 2011; 8(65):19 pp.

Bissig KD et al. Human liver chimeric mice provide a model for hepatitis B and C virus infection and treatment. J Clin Invest. 2010; 120(3): 924-30.

Heckel JL et al. Neonatal bleeding in transgenic mice expressing urokinase-type plasminogen activator. Cell. 1990; 62(3): 447-456.

Vanwolleghem T et al. Factors determining successful engraftment of hepatocytes and susceptibility to hepatitis B and C virus infection in uPA-SCID mice. Journal of Hepatology. 2010; 53(3): 468-476.

He Z et al. Liver xeno-repopulation with human hepatocytes in Fah-/-Rag2-/- mice after pharmacological immunosuppression. Am J Pathol. Sep. 2010; 177(3): 1311-9.

Ito R et al. Current advances in humanized mouse models. Cellular & Molecular Immunology. 2012; 9: 208-214.

\* cited by examiner

RECOMBINANT NON-HUMAN MAMMALIAN MODEL FOR HEPATITIS INFECTION AND IMMUNOPATHOGENESIS

RELATED APPLICATIONS

This application is a 35 U.S.C. §371 national phase entry of PCT Application PCT/2009/001081, filed Feb. 20, 2009, and published in English on Aug. 27, 2009, as International Publication No. WO 2009/105244, and which claims the benefit under 35 U.S.C. §119(e) of U.S. Provisional Patent Application Ser. No. 61/030,328, filed Feb. 21, 2008, the disclosure of each of which is incorporated herein by reference in its entirety.

STATEMENT OF GOVERNMENT SUPPORT

This invention was made with Government support under grants R21-CA99939 and RO1-AI41356 from the National Institutes of Health. The United States Government has certain rights to this invention.

FIELD OF THE INVENTION

The present invention concerns transgenic non-human animals and methods of making and using the same.

BACKGROUND OF THE INVENTION

Liver disease induced by hepatitis C virus (HCV) and hepatitis B virus (HBV) is a global health problem. The World Health Organization estimates that 350-400 million people are chronically infected, and about one million die annually due to chronic hepatitis, cirrhosis or liver cancer. Another 200 million people are infected by HCV, of whom 70%-85% will become chronically infected. HBV and HCV infection is the leading cause of liver disease in Asia. In Western countries, HCV infection is the leading indication for liver transplantation and a major cause of liver cancer.

The liver is a unique organ for immune responses and viruses/tumors (for review, see Crispe, I. N. 2003. Hepatic T cells and liver tolerance. Nat Rev Immunol 3:51-62). The liver intrinsically dampens the immune responses to foreign antigens filtering through it from the intestines. An allogeneic liver transplant is often accepted with minimal or no immune suppression. Tumors with tumor-specific antigens can metastasize to and survive in the liver in immuno-competent patients. Infection of hepatocytes by viruses such as HCV often leads to specific immune tolerance to the virus, and to chronic or persistent infection (Bowen et al. 2005. Adaptive immune responses in acute and chronic hepatitis C virus infection. Nature 436:946-52; Grakoui et al. 2003. HCV persistence and immune evasion in the absence of memory T cell help. Science 302:659-62).

Although the liver may provide an immunologically privileged site for infections, most infections in the liver, such as HAV and MHV, and HBV in adults, are effectively cleared and accompanied with lasting protective immunity. It is unusual that greater than 80% of HCV infection in immuno-competent hosts leads to persistent infection. HCV-encoded factors and/or unique host cell tropism may contribute to the efficient immune evasion and HCV persistence.

The liver consists of unique subsets of antigen presenting cells and lymphocytes. In addition to dendritic cells, a large number of liver macrophages (or Kupffer cells) and sinusoidal endothelial cells in the liver also have efficient phagocytosis activity and express various levels of MHC and T cell costimulatory molecules. However, they often show suboptimal T cell activation activity in vivo (Everett et al. 2003. Kupffer cells: another player in liver tolerance induction. Liver Transpl 9:498-9; Parker et al. 2005. Liver immunobiology. Toxicol Pathol 33:52-62; Racanelli et al. 2006. The liver as an immunological organ. Hepatology 43:S54-S62; Sun et al. 2003. Hepatic allograft-derived Kupffer cells regulate T cell response in rats. Liver Transpl 9:489-97; Wiegard et al. 2005. Murine liver antigen presenting cells control suppressor activity of CD4+ CD25+ regulatory T cells. Hepatology 42:193-9). The liver also contains lymphoid cells with unique features. Up to 25% of lymphoid cells belong to the NKT cell population that expresses TCR as well as NK markers. Their function in the liver is not clear, but they have been implicated in clearing infections in the liver (Behar et al. 1999. Susceptibility of mice deficient in CD1 D or TAP1 to infection with Mycobacterium tuberculosis. J Exp Med 189: 1973-80; Skold et al. 2003. Role of CD1d-restricted NKT cells in microbial immunity. Infect Immun 71:5447-55).

HCV/HBV coinfection with the HIV-1 virus, which is highly prevalent among intravenous drug users, leads to accelerated liver disease progression (Bani-Sadr et al. 2006. Hepatic steatosis in HIV-HCV coinfected patients: analysis of risk factors. Aids 20:525-31; Brau, N. 2003. Update on chronic hepatitis C in HIV/HCV-coinfected patients: viral interactions and therapy. Aids 17:2279-90; Sabin et al. 2004. HIV/HCV coinfection, HAART, and liver-related mortality. Lancet 364:757-8; author reply 758). Liver failure is increasingly affecting HIV-1/HCV-coinfected patients, as their AIDS-free survival is being prolonged by highly active antiretroviral therapy (HAART).

The available treatment for HCV infection is far from optimal, and HIV-1/HCV-coinfected patients show even worse responses to pegylated interferon plus rivabirin than HCV-monoinfected patients (Sola et al. 2006. Poor response to hepatitis C virus (HCV) therapy in HIV- and HCV-coinfected patients is not due to lower adherence to treatment. AIDS Res Hum Retroviruses 22:393-400). There is a great need for alternative treatment options for hepatitis infection.

A relevant small animal model for research on HCV/HBV infection and pathogenesis is therefore needed. However, HCV fails to infect murine cells due to blocks at multiple steps of the HCV life cycle. HCV and HBV can only infect, establish chronic infection and to lead to liver pathogenesis in humans. Only a reduced chronic infection and immunopathogenesis are observed in chimpanzees, which provides the only current non-human animal model for HCV infection (Pietschmann et al. 2003. Tissue culture and animal models for hepatitis C virus. Clin Liver Dis 7:23-43).

The Alb-uPA transgenic mouse, developed in 1990 by Heckel et al. (1990. Neonatal bleeding in transgenic mice expressing urokinase-type plasminogen activator. Cell 62:447-56) to study plasminogen hyperactivation and therapeutic protocols to prevent bleeding, contains a tandem repeat of four murine uPA genes under the control of an albumin promoter. The transgene overexpression results in profound hypo-fibrinogenemia and accelerated hepatocyte death. Homozygous animals can be rescued by transplantation of murine or human hepatocytes, which undergo rapid proliferation to replace the dying hepatocytes (Mercer et al. 2001. Hepatitis C virus replication in mice with chimeric human livers. Nat Med 7:927-33; Meuleman et al. 2005. Morphological and biochemical characterization of a human liver in a uPA-SCID mouse chimera. Hepatology 41:847-56; Meuleman et al. 2006. Immune suppression uncovers endogenous cytopathic effects of the hepatitis B virus. J Virol 80:2797-807). Transplanted human hepatocytes can be infected with HBV and HCV (Mercer et al. 2001. Hepatitis C virus replication in mice with chimeric human livers. Nat Med 7:927-33; Meuleman et al. 2006. Immune suppression uncovers endogenous cytopathic effects of the hepatitis B virus. J Virol 80:2797-807).

A molecularly cloned, cell culture-produced hepatitis C virus (HCVcc) genome has been recently shown to support efficient replication in vitro (Blight et al. 2000. Efficient initiation of HCV RNA replication in cell culture. Science 290:1972-4; Lindenbach et al. 2005. Complete replication of hepatitis C virus in cell culture. Science 309:623-6) and in vivo (Lindenbach et al. 2006. Cell culture-grown hepatitis C virus is infectious in vivo and can be recultured in vitro. Proc Natl Acad Sci USA 103:3805-9). The HCVcc is infectious in uPA-SCID mice reconstituted with human hepatocytes, and infection can be serially passaged to a naïve animal.

Infectivity of HCV can be studied in the uPA-SCID mice transplanted with human hepatocytes (Kneteman et al. 2006. Anti-HCV therapies in chimeric scid-Alb/uPA mice parallel outcomes in human clinical application. Hepatology 43:1346-53; Lindenbach et al. 2005. Complete replication of hepatitis C virus in cell culture. Science 309:623-6; Mercer et al. 2001. Hepatitis C virus replication in mice with chimeric human livers. Nat Med 7:927-33; Meuleman et al. 2005. Morphological and biochemical characterization of a human liver in a uPA-SCID mouse chimera. Hepatology 41:847-56). However, immuno-pathogenesis cannot because uPA mice have no immune system. In addition, the uPA-SCID mouse is very sick and not suitable for many studies.

The RagFahγC TKO mouse also allows efficient engraftment of human hepatocytes in a uPA transgene-dependent fashion (Azuma et al. 2007. Robust expansion of human hepatocytes in Fah(-/-)/Rag2(-/-)/Il2rg(-/-) mice. Nat Biotechnol 25:903-10). In the B6 Rag/γC DKO background, the fumarylacetoacetate hydrolase (Fah) mutation is crossed to generate the RagFahγC triple KO mice. After pretreatment with a urokinase-expressing adenovirus, these animals could be highly engrafted with human hepatocytes. However, due to lack of a functional immune system (which is not suitable for human immune system development), it is not possible to study HCV/HBV immunopathogenesis in these uPA-SCID/-TKO models.

Thus, a mouse model having both a functional human immune system and a human liver is needed to study HCV/HBV infection, immune responses and pathogenesis.

Two human-mouse chimera models with human lymphoid organs implanted in immunodeficiency mice have been constructed to study HIV-1 infection in vivo. The hu-PBL-SCID mouse is limited due to its lack of human hemato-lymphoid organs and its selective engraftment of xeno-reactive human T cells (Mosier et al. 1988. Transfer of a functional human immune system to mice with severe combined immunodeficiency. Nature 335:256-9; Mosier et al. 1991. Human immunodeficiency virus infection of human-PBL-SCID mice. Science 251:791-4; Tary-Lehmann et al. 1994. Anti-SCID mouse reactivity shapes the human CD4+ T cell repertoire in hu-PBL-SCID chimeras. J Exp Med 180:1817-27). The SCID-hu Thy/Liv mouse has an intact human thymus organ, which allows investigation of HIV-1 pathogenesis in the thymus (McCune et al. 1991. The SCID-hu mouse: a small animal model for HIV infection and pathogenesis. Annu Rev Immunol 9:399-429; McCune et al. 1988. The SCID-hu mouse: murine model for the analysis of human hematolymphoid differentiation and function. Science 241:1632-9; Su et al. 1995. HIV-1-induced thymocyte depletion is associated with indirect cytopathogenicity and infection of progenitor cells in vivo. Immunity 2:25-36). However, no human B or myeloid cells and very low levels of human T cells are detected in the peripheral organs or blood. Therefore, no significant primary human immune responses are observed in the model.

A more relevant in vivo non-human animal model that allows hepatitis infection as well as hepatitis and HIV co-infection is, therefore, needed.

SUMMARY OF THE INVENTION

Provided herein is a recombinant non-human mammal (e.g., a mouse) comprising: (a) an immune system comprising, consisting of, or consisting essentially of: human T cells, human B cells, human natural killer cells, human monocytes and macrophages and human dendritic cells, so that the mammal expresses a human immune system phenotype; and (b) a liver comprising, consisting of, or consisting essentially of human hepatocytes, so that the mammal expresses a human liver phenotype. In some embodiments, the human liver cells comprise at least 20, 30, 40 or 50% of said liver of said mammal (by weight, by volume and/or by number of cells) (measured, e.g., by human albumin staining). In some embodiments, the mammal is a Rag2-gammaC double knockout mammal. In some embodiments, the mammal comprises non-human cells that contain a liver-specific promoter (e.g., an albumin promoter) operatively associated with a nucleic acid encoding a product with inducible toxicity to said non-human cells (e.g., FKBP-Caspase 8). In some embodiments, the mammal is infected with a virus, e.g., HIV-1 virus, a hepatitis virus (e.g., HBV or HCV), or both.

Also provided herein are methods of screening a compound for activity in treating hepatitis, comprising: administering a test compound to a recombinant non-human mammal as described herein; and then detecting the presence or absence of said activity in said mammal (e.g., by biochemical assay), said presence of said activity in said mammal indicating that said compound has activity in treating hepatitis.

Further provided are methods of making a non-human transgenic mammal comprising an immune system, said immune system comprising: human T cells, human B cells, human natural killer cells, human monocytes and macrophages and human dendritic cells, so that the mammal expresses a human immune system phenotype; and a liver comprising human hepatocytes, so that the mammal expresses a human liver phenotype. The methods comprise the steps of: a) providing a BalbC/Rag2$^{-/-}$γ$_c$$^{-/-}$ double knockout transgenic mammal (optionally further comprising an Alb-FKBP-Casp8 transgene); b) transplanting human CD34+ hematopoietic stem cells into said double knockout transgenic mammal, wherein said stem cells differentiate into human T cells, human B cells, human natural killer cells, and human dendritic cells in said transgenic mammal; and c) transplanting human liver cells into said double knockout transgenic mammal, wherein said liver cells form human hepatocytes in said liver of said transgenic mammal. In some embodiments, the human CD34+ hematopoietic stem cells and the human liver cells are autogeneic. In some embodiments, the human liver cells comprise human parenchyma hepatoblasts. In some embodiments, the human CD34+ hematopoietic stem cells and the human liver cells are transplanted simultaneously. In some embodiments, the transplanting steps are carried out when the transgenic mammal is from 0 to 10 days old. In some embodiments, the methods further comprise the step of administering (e.g., by injection) a c-Met agonist (e.g., an anti-C-met antibody) selective for human c-Met to said transgenic animal.

Methods of making fusion cells useful for the production of human monoclonal antibodies are also provided, said method comprising: isolating a human antibody-secreting B lymphocyte from a recombinant non-human mammal (e.g., from a spleen or lymph node), said mammal comprising: (a) an immune system comprising: human T cells, human B cells, human natural killer cells, human monocytes and macrophages and human dendritic cells, so that said mammal expresses a human immune system phenotype; and (b) a liver comprising human hepatocytes, so that said mammal expresses a human liver phenotype; and fusing said antibody-secreting B lymphocyte with immortal cells (e.g., human or mouse myeloma cells) to form said fusion cells. In some embodiments, the mammal is infected with a virus, e.g., HIV-1 virus, a hepatitis virus (e.g., HBV or HCV), or both.

Also provided is the use of a non-human transgenic mammal, cell or cell culture as described herein for the preparation of a composition or medicament for carrying out a method of treatment as described herein, or for making an article of manufacture as described herein.

DETAILED DESCRIPTION OF THE PREFERRED EMBODIMENTS

Figure 1A:
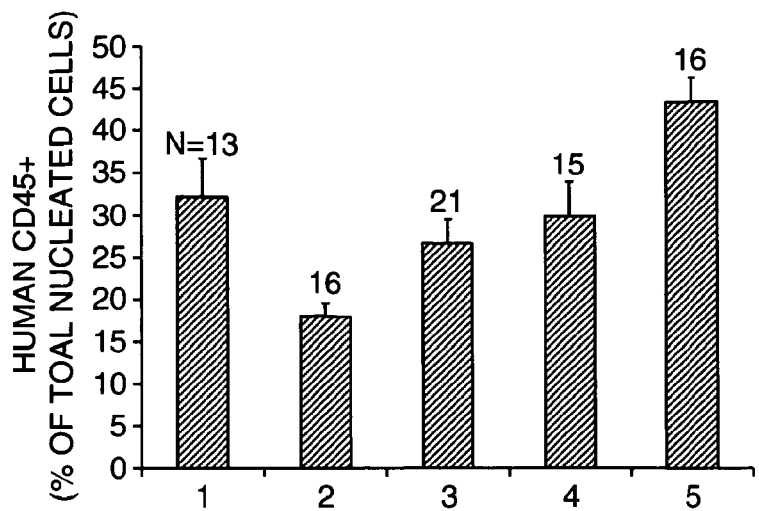
FIG. 1. Long-term, stable human hemato-lymphopoiesis in HSC-DKO Mice. Human fetal liver CD34+ cells were injected intra-hepatically in newborn (1-3 days old) DKO mice. At 12-50 weeks post transplant, the human $CD45^+$, murine $CD45^-$ cells in PBMC, lymph node (LN), spleen, bone marrow and thymus were analyzed by multi-color FACS. A: Human CD45 reconstitution (12-16 weeks old) in 5 cohorts of DKO-hu HSC mice from 5 independent donor fetal livers. Shown is average % human CD45+ cells in PB of reconstituted DKO-hu HSC mice. Error bars indicate standard errors of each cohort (n=numbers of mice/cohort). B: Human cells reconstitution in PBMC of the transplanted mice. Individual bars represent percentage of human CD45+ cells of 12 mice from the same cohort (14 weeks post transplant). The darker inside bars indicate the portion of human CD3+CD4+ cells. C: Total number of splenocytes and thymocytes from a typical DKO-hu cohort (n=12) is compared to wild type and DKO mice. Error bars are standard deviations. D: Stable reconstitution of naïve and resting human T cells. Human T cells from a DKO-hu mouse at 50 weeks are analyzed for expression of CD45RO and CD69. E/F: Human CD4+ T cells purified from DKO-hu mice or from human PBMC are stimulated with various doses of anti-CD3 mAb with (solid squares) or without (open squares) anti-CD28 mAb. Human T proliferation is measured by 3-H thymidine incorporation for 16 hr after 3 days post co-culture. G: Tolerization of human T cells to both BalbC host cells and to the donor human cells in DKO-hu HSC mice. Splenocytes from DKO-hu mouse cohort A (A1 and A2), cohort B (B) and untransplanted DKO mouse (DKO) are prepared and mixed in culture in triplicates at 2×10e5 total cells/well (in mixed cultures, 1×10e5 cells per donor cells are used). Similar human cells (about 50%) are engrafted in A1, A2 and B DKO-hu mice. Only A1/B and A2/B co-culture show significant proliferation (p<0.05) in the MLR assay. H: DKO-hu mice are vaccinated with Ova protein and Ova-specific T cell recall response is measured at 3 weeks post vaccination. Splenocytes from vaccinated or control "cohort-mate" mice are compared for response to Ova protein challenge in vitro. Human T cell proliferation is measured as above.

The present invention is explained in greater detail below. The disclosures of all United States patent references cited herein are to be incorporated by reference to the extent they are consistent with the disclosure herein.

As used herein in the description of the invention and the appended claims, the singular forms "a," "an" and "the" are intended to include the plural forms as well, unless the context clearly indicates otherwise. Furthermore, the terms "about" and "approximately" as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" or "/" refers to and encompasses any and all possible combinations of one or more of the associated listed items, as well as the lack of combinations when interpreted in the alternative ("or").

An improved non-human animal model of hepatitis infection is provided herein. The model has well-studied hemato-lymphoid cells and liver target cells which are human, and HCV can establish infection and lead to T cell tolerance with similar features of T cell responses as in HCV infected human or chimps. In some embodiments, the non-human animal is genetically inbred, inexpensive and can be manipulated by genetic, immunological and pharmacological means.

The model is also useful for studying HCV/HBV and HIV co-infection and for identifying or confirming therapeutic strategies for controlling hepatitis diseases. The model is further useful for studying human liver development/regeneration, identifying and screening compounds, and determining the pharmacokinetics of preclinical drugs.

Besides infection and immuno-pathogenesis, the model is useful to study human liver stem cells, hepatocyte development/liver regeneration and autoimmune hepatitis. First, different subsets of human hepatocyte progenitors can be tested. Second, the non-human animal is efficiently reconstituted with a functional human immune system with T, B and myeloid cells in lymphoid organs including liver. These human immune cells are present as normal resting cells and respond to antigenic stimulation in vitro or in vivo (Gimeno et al. 2004. Monitoring the effect of gene silencing by RNA interference in human CD34+ cells injected into newborn RAG2-/-gammac-/- mice: functional inactivation of p53 in developing T cells. Blood 104:3886-93; Traggiai et al. 2004. Development of a human adaptive immune system in cord blood cell-transplanted mice. Science 304:104-7; and FIG. 3). The model is further useful for human liver regeneration, immuno-pathogenesis and immune-based therapeutics. With the model including a human liver, drug liver toxicity, metabolism, and pharmacokinetics may also be tested.

"DKO-hu HSC" as used herein refers to the RAG2-/- γC-/- double knockout non-human mammal (with the suicidal transgene) comprising a human immune system formed from human hematopoietic stem cell administration.

"DKO-hu HSC/Hep" as used herein refers to the DKO-hu HSC non-human mammal (with the suicidal transgene) further comprising human liver cells (e.g., human hepatocytes).

"Hepatitis" is an inflammation of the liver characterized by the presence of inflammatory cells in the liver. Acute hepatitis lasts for less than 6 months, while chronic hepatitis lasts 6 months or longer. Causes of hepatitis include, but are not limited to, certain viruses, toxins (e.g., alcohol), infections elsewhere in the body, an autoimmune response, metabolic disease, etc. Hepatitis caused by viruses include, but are not limited to, Hepatitis A, Hepatitis B, Hepatitis C, Hepatitis D (as a co-infection with Hepatitis B virus), Hepatitis E, Hepatitis F, Hepatitis G, Herpes simplex, Cytomegalovirus, Epstein-Barr, yellow fever, adenovirus, etc.

"Hepatitis C virus" or "HCV" is the virus that causes Hepatitis C. Acute Hepatitis C symptoms, if present, are mild, and therefore the infection is often not diagnosed at this early stage. About 20-30% of people infected with HCV will clear the virus from their systems during the acute phase (i.e., the first 6 months after infection). The remaining 70-80% will develop a chronic infection (i.e., lasting 6 months or longer). Symptoms during the chronic phase are normally also mild, until significant scarring of the liver has occurred. Once chronic, there is little chance of clearing the virus without medical treatment. Co-infection of Hepatitis C with HIV, which is also a blood-borne virus, is common in the United States, particularly among intravenous drug users.

"Hepatitis B virus" or "HBV" is the virus that causes Hepatitis B. Children are more susceptible than adults to develop a chronic HBV infection. While more than 95% of adults are able to clear the virus without medical treatment, 70% of children ages 1-6, and only 5% of newborns who acquire HBV from their mothers can clear the infection without treatment. Those who do not clear the virus become chronic carriers.

"HIV" is the human immunodeficiency virus. It is a retrovirus that can lead to acquired immune deficiency syndrome (AIDS), a condition in which the immune system is compromised and the body is susceptible to opportunistic diseases that can be life-threatening. HIV primarily infects immune system cells, and leads to a decrease in the number of CD4+ T cells, which are important for cell-mediated immunity. The most common strain of HIV is HIV-1. A second strain, HIV-2, is also known.

"Transplanting," "engrafting" or "grafting" is the placement of cells or tissue originating from one animal (e.g., a human) into another (e.g., a mouse). In some embodiments cells are autogeneic (i.e., from the same individual animal or subject), isogeneic (i.e., a genetically identical but different animal or subject, e.g., from an identical twin, also known as syngeneic), allogeneic (i.e., from a non-genetically identical member of the same species) or xenogeneic (i.e., from a member of a different species, also known as xenografting). In some embodiments, stem/progenitor cells are engrafted into the non-human animal.

"Infectivity" is the characteristic of an infectious agent (i.e., an agent that causes infection) that enables it to enter, survive and multiply in a suitable host. Similarly, an "infection" is the invasion by and multiplication of one or more pathogenic microorganisms (e.g., viruses, bacteria, etc.) in a bodily part or tissue, which may produce subsequent tissue injury and progress to overt disease, or the pathological state resulting from having been infected by such microorganisms.

"Immunopathogenesis" includes the cellular and mechanistic events underlying the typical course of development of an infection or disease that involves the immune response or the products of an immune response. In some embodiments, immunopathogenesis includes a dysfunction of the immune response (e.g., HIV infection lowers T cell count).

A "human immune system phenotype" is an immune system of a non-human animal that includes all or essentially all human cells of the hematopoietic lineages, including adaptive immune system cells such as T cells, B cells, dendritic cells, natural killer (NK) cells, monocytes and macrophages, etc.

"Human" cells include, but are not limited to, cells that are directly isolated from human tissue as well as cells derived from human cells, e.g., stem cells (such as hematopoietic stem cells) differentiated into immune system cells (e.g., in a non-human host animal, in vitro, etc.).

"Hematopoietic stem cells" are stem cells typically found in bone marrow, cord blood, fetal liver and/or mobilized peripheral blood that can differentiate into all types of blood cells, including myeloid and lymphoid lineages. In some embodiments, hematopoietic stem cells are directly delivered (e.g., by direct injection) into the liver of the animal (e.g., newborn mice).

The "adaptive immune system" includes immune cells that are able to remember and recognize antigens or pathogens that had previously evoked an immune response, and are thereby able to mount a stronger response upon subsequent exposures, giving rise to "immunity" to a pathogen.

A "lymphocyte" is a type of white blood cell typically found in vertebrates. Large granular lymphocytes include the natural killer (NK) cells, which are involved in innate immunity. Small lymphocytes include the T cells and B cells, which are involved in adaptive immunity. T cells (e.g., helper T cells, cytotoxic T cells) are typically involved in the cell-mediated immune response, while B cells are typically involved in the humoral immune response. T cells and B cells typically recognize non-self antigens presented on the surface of cells and elicit an immune response tailored to the non-self antigens. After activation, T cells and B cells typically leave behind memory cells that can elicit a stronger response if the antigens are again detected.

A "human liver phenotype" is a liver organ of a non-human animal that includes human liver cells. "Human liver cells" are cells that normally form the liver organ in humans, and include, but are not limited to, human hepatoblasts, hepatocytes, hepatic stellate cells, Kupffer cells, sinusoidal endothelial cells, lymphoid cells, etc.

"Hepatocytes" are the primary cells of the liver organ. Human liver cells may also) include stem/progenitor cells of the liver (e.g., hepatocyte progenitor cell). "Hepatoblasts" are fetal liver stem-progenitor cells.

In some embodiments, human liver cells (e.g., hepatoblasts) are directly delivered (e.g., by direct injection) into the liver of the animal (e.g., newborn mice). Other methods for the introduction of human liver cells into a non-human animal are known in the art. See, e.g., U.S. Pat. No. 7,161,057 to Kneteman et al., which discusses infusing hepatocytes into the spleen of the animal.

In some embodiments, the liver organ of the non-human animal comprises at least 10, 20, 30, 40, or 50% of one or more types of human liver/leukocyte cells (e.g., hepatocytes) by weight, by volume and/or by cell count. In some embodiments, the liver organ comprises at least 60, 70 or 80% of human liver/leukocyte cells by weight, by volume or by cell count.

"Isolated" signifies that the cells are placed into conditions other than their natural environment. However, the term "isolated" does not preclude the later use of these cells thereafter in combinations or mixtures with other cells.

"Non-human animals" of the present invention are, in general, mammals including primates, such as monkeys, more preferably rodents, and are more particularly mice and rats. Animals may be male or female, and may be of any age including adult. In some embodiments animals are laboratory animals (e.g., non-human primates, rodents, dogs, pigs, birds, etc.). In some embodiments animals are mammalian laboratory animals.

A "recombinant" or "transgenic" non-human animal refers to a non-human animal that has a genome or genetic material that is augmented or altered in some fashion with a construct comprising a recombinant nucleic acid (e.g., a "transgene") that is introduced into one or more of the somatic and/or germ cells of the mammal. The nucleic acid or portions thereof may be, for example, of the same species (homologous) or of another species (heterologous) with respect to the host mammal.

A "recombinant" nucleic acid refers to a nucleic acid that has been manipulated in vitro, for example, by molecular biology techniques as described herein and as known in the art.

A "knockout" of a target gene refers to an alteration in a host cell genome that results in altered expression of the target gene (typically a reduction in expression), e.g., by introduction of a mutation into a coding or noncoding region of the target gene, which mutation alters expression of the target gene. Mammals may be heterozygous or homozygous with respect to the mutation or insertion that causes the knockout.

"Wild type" gene or protein sequences of a given species are those DNA or protein sequences that are generally accepted in the art as being the most highly conserved within or across species.

By the term "express" or "expression" of a nucleic acid coding sequence, it is meant that the sequence is transcribed, and optionally, translated. Transcription can be measured by any means well known by those of skill in the art, e.g., measuring the relative levels of mRNA expression (e.g., with a northern blot, quantitative PCR, etc.). Typically, expression of a coding region will result in production of the encoded protein or polypeptide (measured by, e.g., western blot).

The production of transgenic animals is known and can be carried out in accordance with known techniques or variations thereof which will be apparent to those skilled in the art, for example, as disclosed in: U.S. Pat. No. 7,022,893 to Takeda et al. and U.S. Pat. No. 6,218,595 to Giros et al., as well as U.S. Pat. No. 6,344,596 to W. Velander et al. (American Red Cross); U.S. Pat. No. 6,339,183 to T. T. Sun (New York University); U.S. Pat. No. 6,331,658 to D. Cooper and E. Koren; U.S. Pat. No. 6,255,554 to H. Lubon et al. (American National Red Cross; Virginia Polytechnic Institute); U.S. Pat. No. 6,204,431 to P. Prieto et al. (Abbott Laboratories); U.S. Pat. No. 6,166,288 to L. Diamond et al. (Nextran Inc., Princeton, N.J.); U.S. Pat. No. 5,959,171 to J. M. Hyttinin et al. (Pharming BV); U.S. Pat. No. 5,880,327 to H. Lubon et al. (American Red Cross); U.S. Pat. No. 5,639,457 to G. Brem; U.S. Pat. No. 5,639,940 to I. Garner et al. (Pharmaceutical Proteins Ltd.; Zymogenetics Inc); U.S. Pat. No. 5,589,604 to W. Drohan et al. (American Red Cross); U.S. Pat. No. 5,602,306 to Townes et al. (UAB Research Foundation); U.S. Pat. No. 4,736,866 to Leder and Stewart (Harvard); and U.S. Pat. No. 4,873,316 to Meade and Lonberg (Biogen).

Human Immune System.

Preferably, the non-human animal has an immune system comprising human immune cells. The transplantation of human CD34+ cells into SCID or NOD/SCID mice leads to the generation of mainly human myeloid and B cells in the mouse bone marrow, but inefficient peripheral engraftment of human cells, especially human T cells (Lapidot et al. 1992. Cytokine stimulation of multilineage hematopoiesis from immature human cells engrafted in SCID mice. Science 255: 1137-41; Larochelle et al. 1996. Identification of primitive human hematopoietic cells capable of repopulating NOD/SCID mouse bone marrow: implications for gene therapy. Nat Med 2:1329-37). More recently, a mouse model with a functional human immune system has been reported. The Rag2-γC double knockout (DKO) mouse lacks T, B and NK cells, and serves as better hosts for engraftment of human cells/tissues. Therefore, in preferred embodiments the non-human animal is a Rag2-γC double knockout (DKO) transgenic non-human animal.

In some embodiments, cord blood CD34+ human HSC are injected directly into the liver of newborn DKO animals (see Traggiai et al. 2004. Development of a human adaptive immune system in cord blood cell-transplanted mice. Science 304:104-7). The new born liver environment appears to support efficient human HSC engraftment and reconstitution of the animal with a functional human immune system in central and peripheral lymphoid organs.

Remarkably, long term human T cell development occurs efficiently in the mouse DKO thymus, and normal human T, B, NK and dendritic cells are readily detected in peripheral lymphoid tissues such as spleen, lymph nodes (LN) and peripheral blood (PB). Importantly, de novo human B and T cell responses are elicited in the hu-HSC-DKO mouse by standard immunization (human TT-specific IgG induction) or infection with the human tumor virus EBV (expansion of EBV-specific CD8 T cells).

Both CCR5 and CXCR4 are expressed on human immature and mature T cells (Zhang et al. 2007. HIV-1 infection and pathogenesis in a novel humanized mouse model. Blood 109:2978-81). DKO-hu HSC mice allow efficient HIV-1 infection with high plasma viremia. High levels of productive infection occur in the thymus, spleen and lymph nodes. Human CD4+ T cells are gradually depleted by HIV-1 in a dose-dependent manner. In addition, HIV-1 infection persists in infected DKO-hu HSC mice for at least 19 weeks, with infectious HIV-1 in lymphoid tissues. Thus, the DKO-hu HSC mouse can serve as a relevant in vivo model to investigate mechanisms of HIV-1 infection and immuno-pathogenesis.

Combined with engrafted human liver cells, the HSC-DKO mouse as described herein can serve as a model to investigate mechanisms of HCV immuno-pathogenesis and how coinfection with HIV-1 may affect HCV replication and/or pathogenesis.

Human Liver Cells.

In preferred embodiments, the non-human mammal comprises human liver cells. Human liver cells may be introduced into the non-human mammal by the procedures provided herein or by procedures known in the art (see, e.g., U.S. Pat. No. 7,161,057 to Kneteman, incorporated by reference herein).

In some embodiments, human hepatoblasts/progenitors are isolated from human fetal liver tissues. Hepatocytes (or parenchyma cells) may be isolated from livers by collagenase digestion as described (Meuleman et al. 2005. Morphological and biochemical characterization of a human liver in a uPA-SCID mouse chimera. Hepatology 41:847-56; Schmelzer et al. 2006. The phenotypes of pluripotent human hepatic progenitors. Stem Cells 24:1852-8). EpCAM, a transmembrane glycoprotein, has been shown to mark human hepatic stem or progenitor cells as it is expressed by hepatic progenitors but not hepatocytes (de Boer et al. 1999. Expression of EpCAM in normal, regenerating, metaplastic, and neoplastic liver. J Pathol 188:201-6). Transplantation of EpCAM+ cells into the liver of mice gives rise to human liver tissue expressing human-liver specific proteins (de Boer et al. 1999. Expression of Ep-CAM in normal, regenerating, metaplastic, and neoplastic liver. J Pathol 188:201-6; Schmelzer et al. 2006. The phenotypes of pluripotent human hepatic progenitors. Stem Cells 24:1852-8).

In some embodiments, approximately one million ($10^6$) CD34+HSC cells are co-transferred with approximately one million ($10^6$) parenchyma cells (comprising human hepatoblasts and/or hepatic stem cells) (105 EpCAM+ hepatoblasts) into the liver of 1- to 3-day-old DKO or AFK8/DKO mice previously irradiated at 400 rad (sublethal). In some embodiments, cells are co-injected in the liver of newborn DKO mice.

Antagonistic Antibody Against c-Met.

To improve human hepatocyte growth, in some embodiments an agonistic antibody against human c-Met (c-Met mAb, mouse IgG1) is used that activates human but not murine c-Met as reported (Ohashi et al. 2000. Sustained survival of human hepatocytes in mice: A model for in vivo infection with human hepatitis B and hepatitis delta viruses. Nat Med 6:327-31).

DKO-Hu HSC/Hep Mice in AFC8/DKO Mice.

Figure 6:
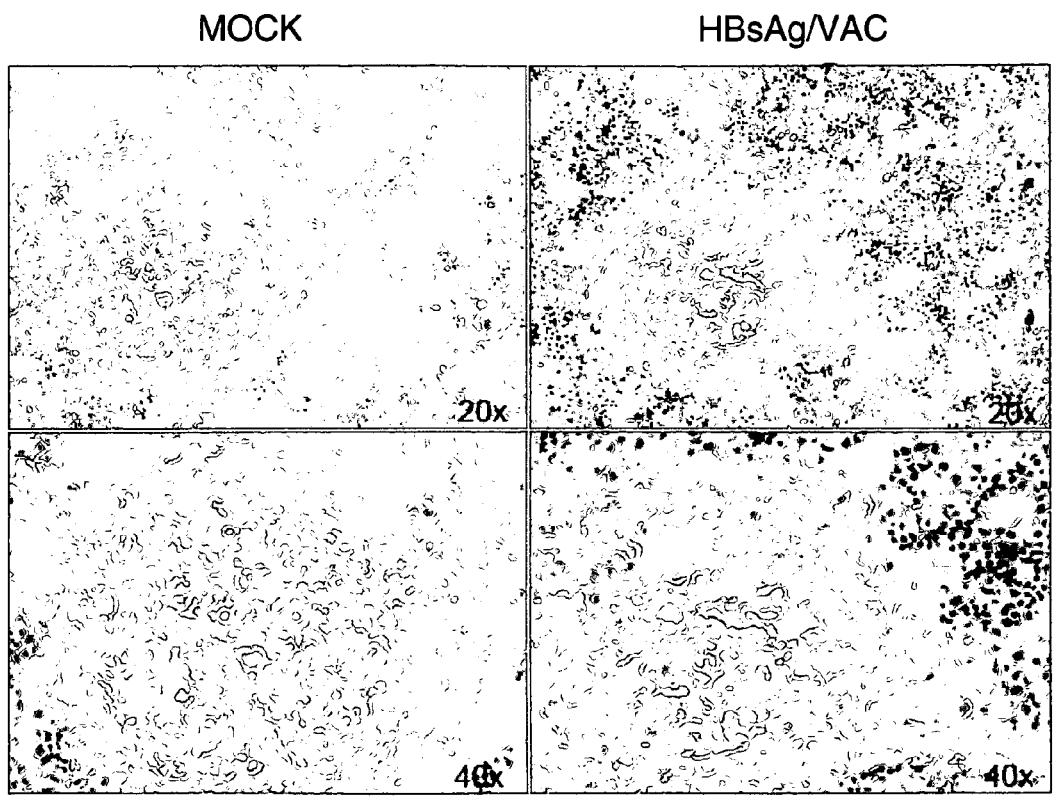
FIG. 6. Spleen tissue of DKO-hu HSC mice at 20× and 40×, Mock versus vaccinated with HBsAg (the surface antigen of HBV).
Figure 7:
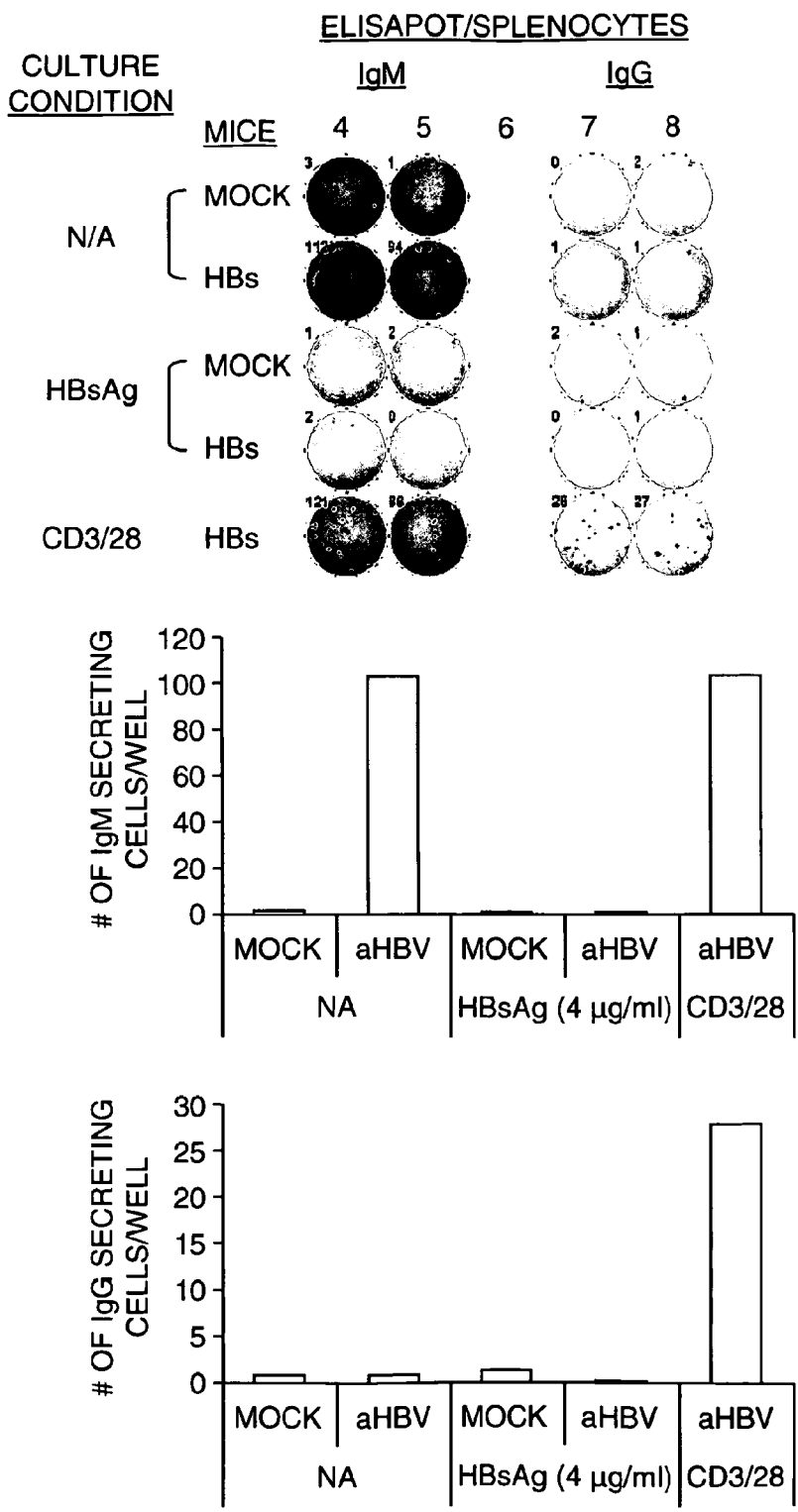
FIG. 7. ELISPOT assay of splenocytes from mock or immunized DKO-hu mice shows that the HBV vaccine induced IgM+ B cells, but not IgG+ B cells. However, IgG+ B cell induction is achieved with anti-CD3/CD28 mAb (T activation) in vitro.

In another embodiment, DKO-hu HSC/Hep mice are generated in an AFC8/DKO background (FKBP-Casp8 gene under control of the albumin promoter, see Heckel et al. 1990. Neonatal bleeding in transgenic mice expressing urokinase-type plasminogen activator. Cell 62:447-56) (FIGS. 6&7). Transfer of adult hepatocytes into uPA-SCID mice has led to efficient engraftment of human hepatocytes (70%) in the chimeric liver (Mercer et al. 2001. Hepatitis C virus replication in mice with chimeric human livers. Nat Med 7:927-33; Meuleman et al. 2005. Morphological and biochemical characterization of a human liver in a uPA-SCID mouse chimera. Hepatology 41:847-56). However, the uPA-SCID or uPA-TKO mouse (Azuma et al. 2007. Robust expansion of human hepatocytes in Fah(-/-)/Rag2(-/-)/Il2rg(-/-) mice. Nat Biotechnol 25:903-10) has no immune system, is difficult to breed and not optimal for most studies. Hepatocytes of the AFC8/DKO mouse can be inducibly depleted with the FKBP dimerizer ligand AP20187 (Burnett et al. 2004. Conditional macrophage ablation in transgenic mice expressing a Fas-based suicide gene. J Leukoc Biol 75:612-23; Pajvani et al. 2005. Fat apoptosis through targeted activation of caspase 8: a new mouse model of inducible and reversible lipoatrophy. Nat Med 11:797-803).

Methods of Screening Compounds.

The present invention also provides methods of screening a compound for activity in treating hepatitis and/or HIV infection. In some embodiments the method comprises administering a test compound to a mammal as described herein, and then detecting the presence or absence of activity in treating and/or preventing hepatitis and/or HIV infection in the mammal. The administering step may be carried out by any suitable technique depending upon the particular compound, including parenteral injection, oral administration, inhalation administration, transdermal administration, etc.

"Treat" refers to any type of treatment that imparts a benefit to a subject, e.g., a subject afflicted with or at risk for developing a disease or condition (e.g., a liver infection and/or HIV/AIDS, etc.). Treating includes actions taken and actions refrained from being taken for the purpose of improving the condition of the subject (e.g., the relief of one or more symptoms), delay in the onset or progression of the disease, disease prevention (e.g., immunization), etc.

Production of Monoclonal Antibodies.

Monoclonal antibodies can be produced in a hybridoma cell line formed according to well-known technique of Kohler and Milstein, (1975) Nature 265:495-97, using a human immune cell isolated from the spleen of a non-human mammal with a human immune system/human liver phenotype for the fusion. For example, human spleen cells are isolated from a non-human animal having a human immune system. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in bacterial cells such as E. coli by recombinant techniques known to those skilled in the art. See, e.g., W. Huse, (1989) Science 246:1275-81.

In some embodiments of the present invention, vaccination of the DKO-hu HSC with a human HBV vaccine induces IgM-producing human B cells, but very low levels of human IgG+ B cells. Human IgG+ B cells can be increased by activating human T cells in the spleen in vitro e.g., with anti-CD3/CD28 mAb. Further, immunization of the non-human animal with a specific protein may induce antigen-specific human IgG producing B cells. In some embodiments, antigen-specific human IgG induction can be enhanced in vivo by using the fusion protein with the antigen and the Fc domain of human IgG.

The present invention is explained in greater detail in the following non-limiting Examples.

Example 1

Stable Reconstitution of DKO Mice with CD34+ HSC (DKO-hu HSC Mice>1 yr)

Figure 1B:
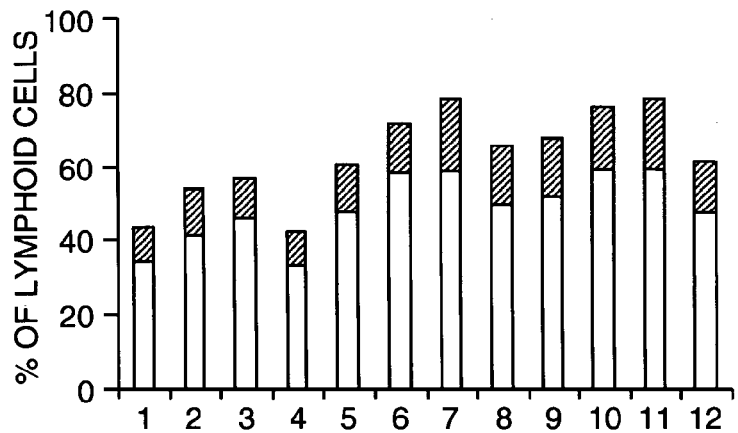
Figure 1C:
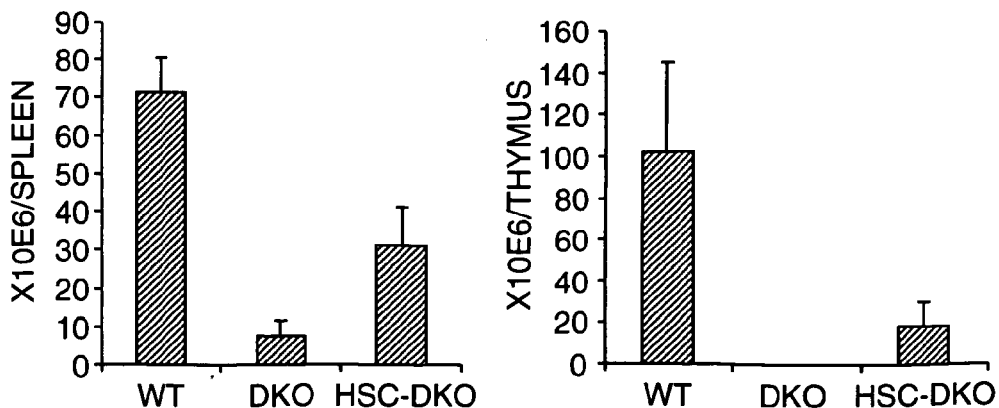
Figure 1D:
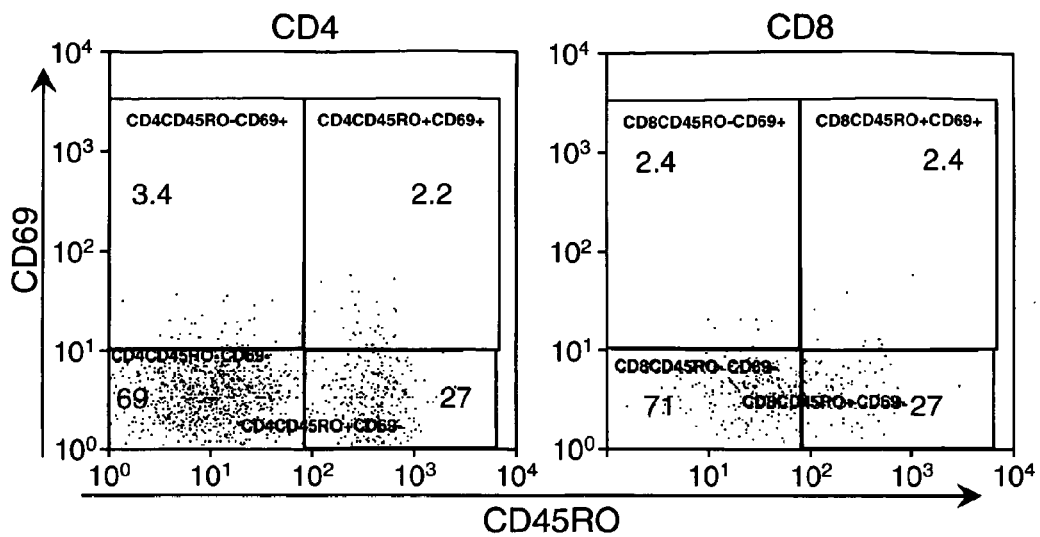
Figure 1E:
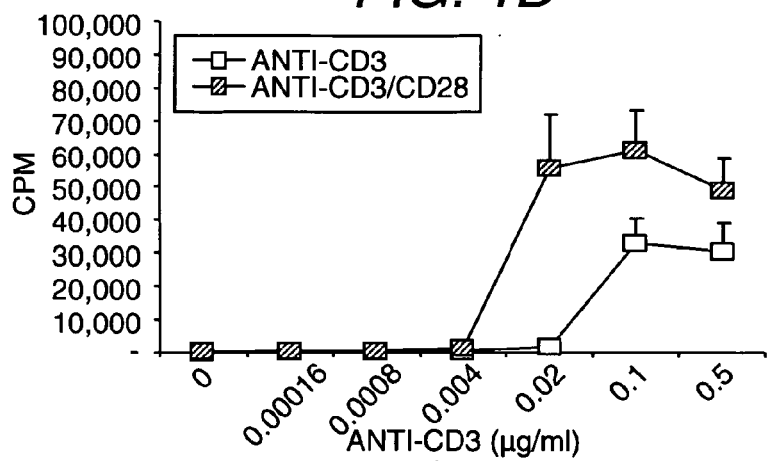
Figure 1F:
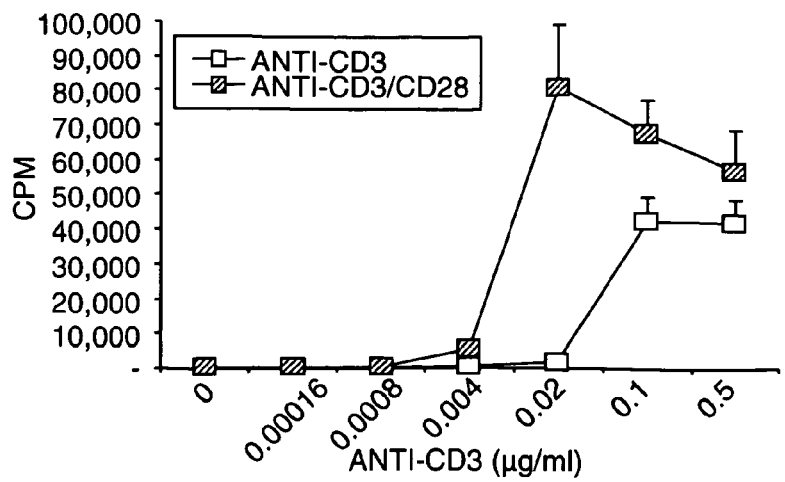

Human fetal liver derived CD34+ HSC ($0.5-1\times10^6$/mouse) were transplanted into newborn DKO mice intra-hepatically. Functional lymphoid organs are formed in the DKO-HSC mice as reported (see Baenziger et al. 2006. Disseminated and sustained HIV infection in CD34+ cord blood cell-transplanted Rag2-/-gamma c-/- mice. Proc Natl Acad Sci U.S.A. 103:15951-6; Traggiai et al. 2004. Development of a human adaptive immune system in cord blood cell-transplanted mice. Science 304:104-7; Zhang et al. 2007. HIV-1 infection and pathogenesis in a novel humanized mouse model. Blood 109:2978-81). Experiments showed that >95% of the transplanted DKO mice have stable human cell engraftment with human CD45+ cells in the blood for at least 50 weeks (FIG. 1A; Zhang et al. 2007. HIV-1 infection and pathogenesis in a novel humanized mouse model. Blood 109: 2978-81; and data not shown). T, B, monocytes, mDC and PDC are stably reconstituted (FIG. 1B and data not shown). About $30\times10^6$ total splenocytes (40% of wild type mice) and $20\times10^6$ thymocytes (20% of wild type mice) are generated in DKO-hu mice (FIG. 1C). Most CD4 and CD8 T cells express a resting naïve phenotype (CD45RO–CD69– and CD62L+ CCR7+, FIG. 1D and data not shown). When their proliferation response to TCR stimulation is compared to human CD4 T cells (FIG. 1F), DKO-hu derived human CD4 T cells (FIG. 1E) show identical response to different doses of anti-CD3 mAb and to CD28 co-stimulation.

Figure 1G:
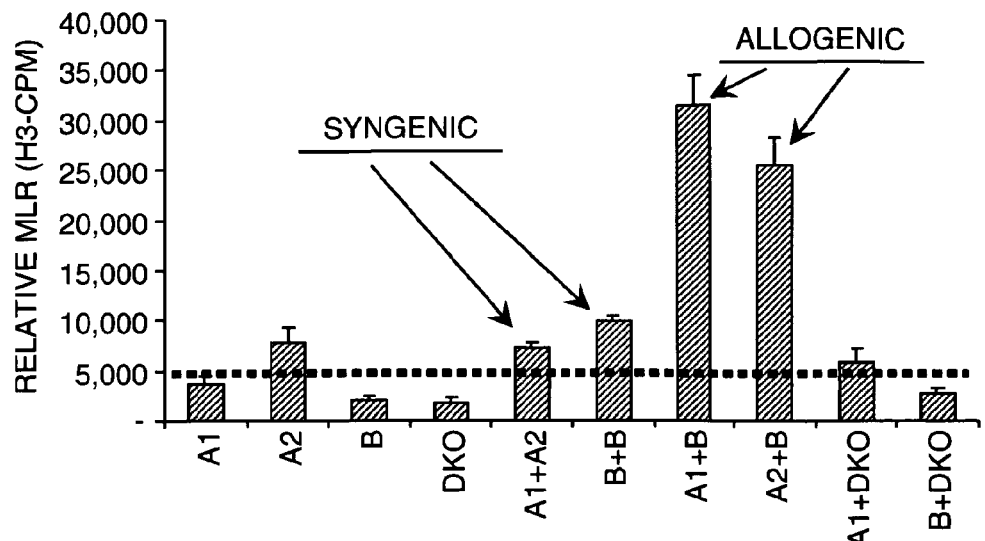
Figure 1H:
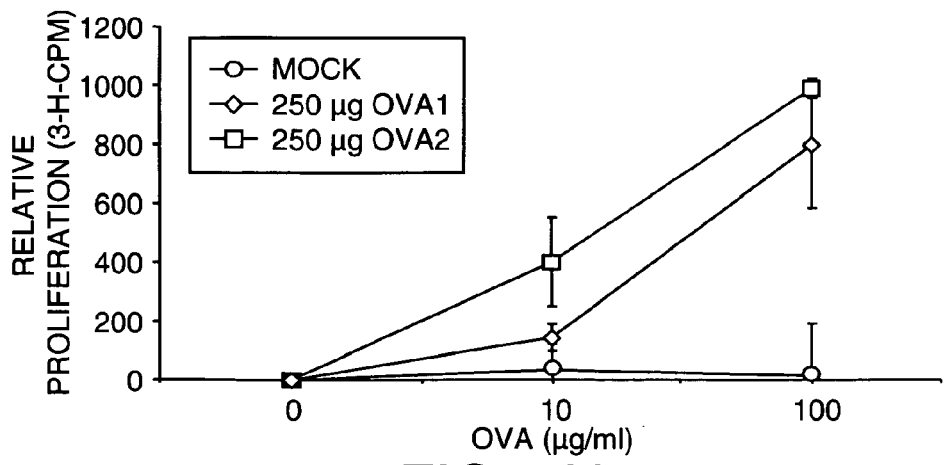

Human T cells are negatively selected by both mouse MHC/APC and human MHC/APC because both human and mouse antigen presenting cells (APC) are detected in the mouse thymus (see Traggiai et al. 2004. Development of a human adaptive immune system in cord blood cell-transplanted mice. Science 304:104-7). Thus, human T cells developed in the DKO-hu HSC mouse are tolerized to both BalbC mouse cells and to human cells from "cohort-mate" DKO-hu mice of the same donor ("inbred/syngeneic" hu-mice) shown by lack of mixed lymphocyte response (MLR) between splenocytes from DKO, A1 and B DKO-hu mice, and between "syngeneic" A1 and A2 DKO-hu mice. However, either A1 or A2 cells react strongly with the "allogeneic" cells from the cohort B DKO-hu mice (FIG. 1G). In addition, immunization of DKO-hu mice with Ova protein induces Ova-specific human T and B cell responses (FIG. 1H and data not shown). Therefore, normal human T and B cells are generated in the DKO-hu mouse.

Example 2

HIV-1 Infection and Pathogenesis in DKO-hu HSC Mice

Figure 2A:
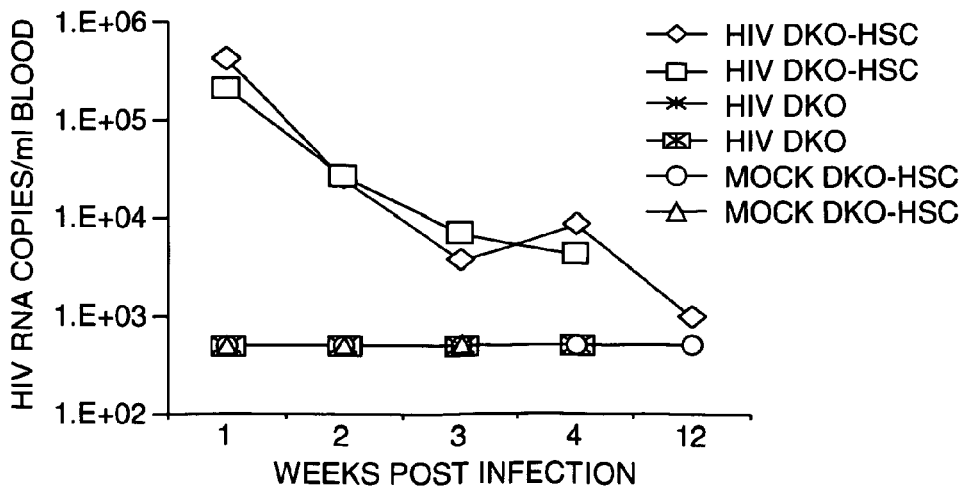
FIG. 2. HIV-1 Replication and Pathogenesis in DKO-hu HSC mice. DKO-hu HSC mice were infected with HIV-R3A or JRCSF (5 ng p24/mouse). DKO mice or mock infected DKO-hu mice are used as controls. For R3A infection, plasma samples were collected at 1, 2, 3, 4 and 12 weeks post infection and HIV genome copy numbers were determined with the Roche Amplicor HIV-1 Monitor Kit (A). (B) FACS analysis of human CD45, CD3, CD4 and CD8 cells from blood samples are performed and relative CD4 depletion is shown (as % CD3+CD4+ or CD4/CD8 ratio). Open symbols are mock controls and solid symbols are HIV-infected mice. (C/D) JRCSF infection is similarly analyzed at 1, 2, 4, 6, and 18 wpi. Shown are data from four infected DKO-hu mice and two mock control mice (D). (E-H) Spleen (ET) or mLN (E/F) samples from DKO-hu mice infected with R3A (E/G, R3A-2 wpi, 3 mocks and 4 R3A-infected mice) or JRCSF (F/H, JRCSF-4 wpi, 4 mocks and 5 JRCSF-infected mice) are summarized for relative CD4 and CD8 in human leukocytes. Error bars are SE. *, p<0.05; **, p<0.01.
Figure 2B:
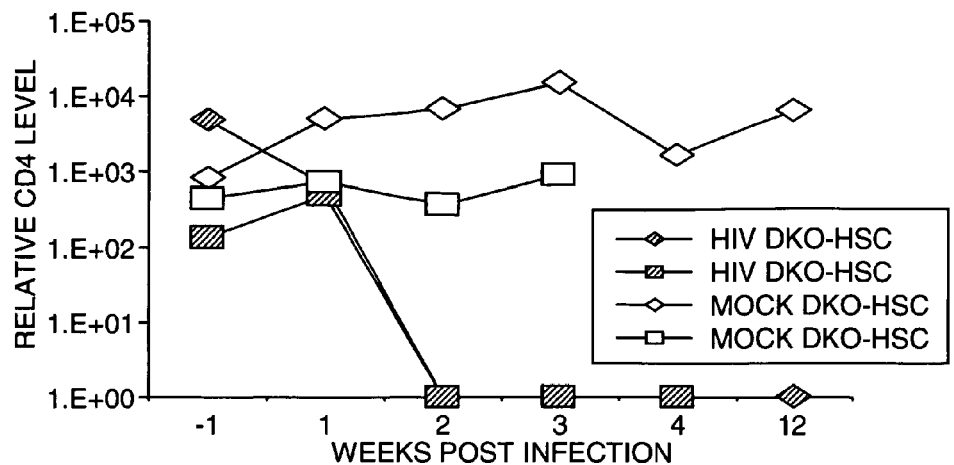
Figure 2C:
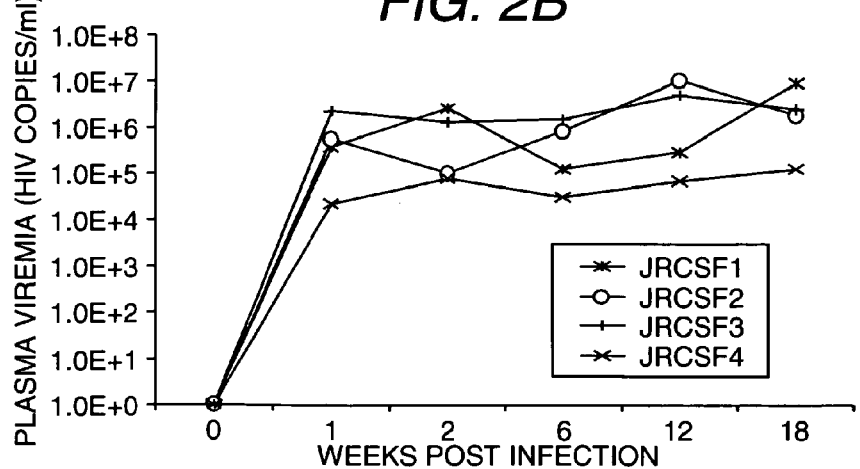
Figure 2D:
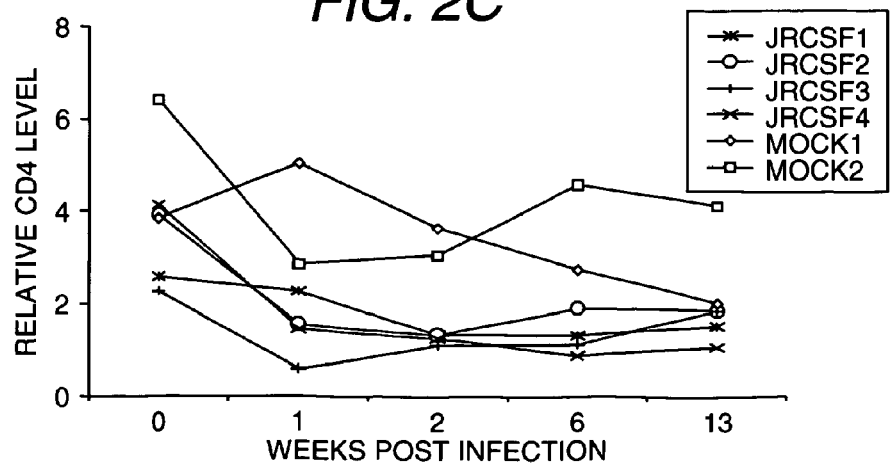
Figure 2E:
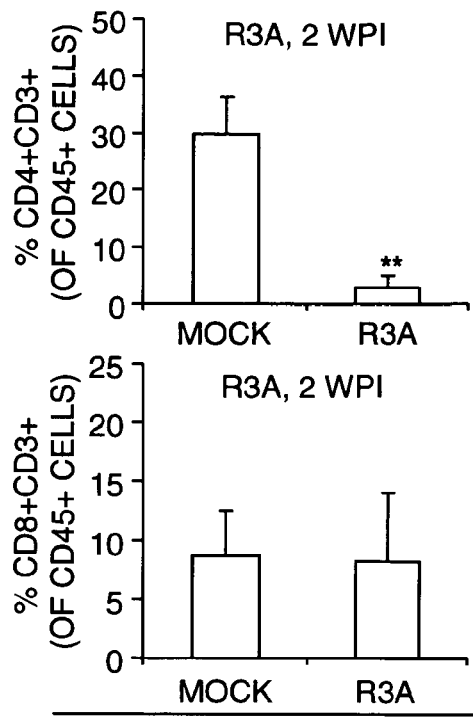
Figure 2F:
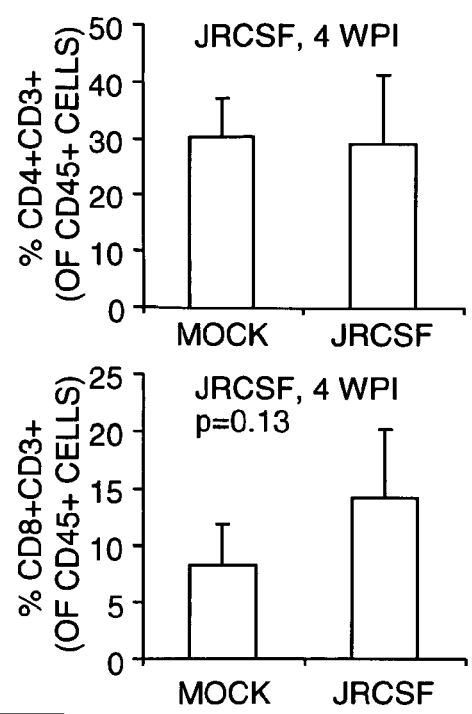
Figure 2G:
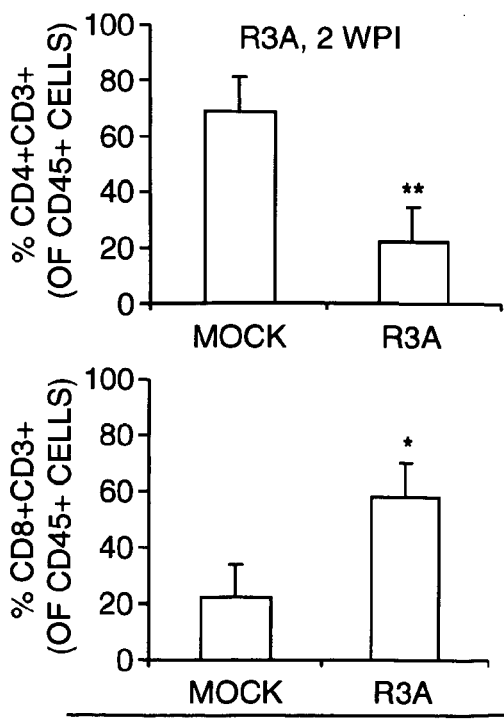
Figure 2H:
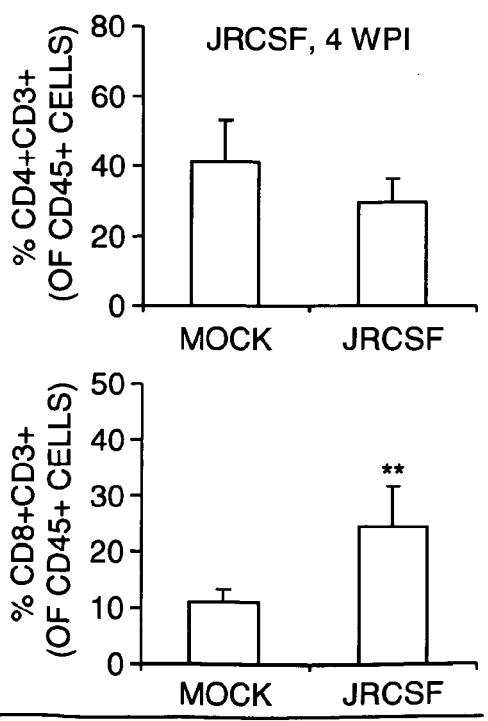

Both CCR5 and CXCR4 are expressed on human immature and mature T cells in DKO-hu mice. DKO-hu HSC mice allow efficient HIV-1 infection with high plasma viremia. High levels of productive infection occur in the thymus, spleen and lymph nodes. Interestingly, both CD45RO+ (memory/effector) and CD45RO– (naïve) CD4T cells are productively infected as stained for HIV gag p24. Human CD4+ T cells are rapidly depleted by a pathogenic HIV-1-R3A (FIG. 2A/B). In addition, HIV-1 infection persists in infected DKO-hu HSC mice for at least 19 weeks, with infectious HIV-1 in lymphoid tissues. DKO-hu mice were also infected with the less pathogenic HIV-1 isolate JRCSF (CCR5-tropic). High levels of HIV replication were detected at 1 to 18 weeks post infection (FIG. 2C). CD4+ T cells in the blood were only slowly decreased but maintained at steady levels for 13-128 weeks (FIG. 2D). When lymphoid organs were analyzed from R3A-(2 wpi) or JRCSF-(4 wpi) samples, R3A infection almost completely depleted human CD4+ T cells in the spleen and dramatically depleted CD4 T cells in mLN, whereas JRCSF infection did not significantly deplete human CD4 T cells in the spleen or mLN (FIG. 2E-H). Interestingly, there is an increase in the CD8 levels in the mLN for both infections.

At 22 wpi with JRCSF, HIV infection is associated with an enlarged spleen and activated HLA-DR+ T cells in DKO-hu mice. CD4 depletion is also observed in lymph node organs and the remaining T cells show activated phenotypes. Therefore, HIV infection leads to immuno-pathogenesis, correlated with hyper-immune activation and inflammation. Indeed, inflammatory cytokines are induced by HIV infection in plasma as well as in lymphoid tissues (data not shown).

Thus, the DKO-hu HSC mouse can serve as a relevant in vivo model to investigate mechanisms of HIV-1 infection and immuno-pathogenesis. HIV-R3A can be used to study acute HIV infection with a rapid CD4 depletion, and JRCSF can be used to study acute HIV infection, immuno-response and chronic HIV infection and immunopathogenesis.

Example 3

Development of the DKO-hu HSC/Hep Mouse

To develop the DKO-hu HSC/Hep mice, we isolated human CD34+ HSC and human hepatoblasts/progenitors from human fetal liver tissues. Hepatocytes (or parenchyma cells) are isolated from livers by collagenase digestion as described (Meuleman et al. 2005. Morphological and biochemical characterization of a human liver in a uPA-SCID mouse chimera. Hepatology 41:847-56; Schmelzer et al. 2006. The phenotypes of pluripotent human hepatic progenitors. Stem Cells 24:1852-8). EpCAM, a transmembrane glycoprotein, has been shown to mark human hepatic stem or progenitor cells as it is expressed by hepatic progenitors but not hepatocytes (de Boer et al. 1999. Expression of Ep-CAM in normal, regenerating, metaplastic, and neoplastic liver. J Pathol 188:201-6). Transplantation of EpCAM+ cells into the liver of mice gave rise to human liver tissue expressing human-liver specific proteins (de Boer et al. 1999. Expression of EpCAM in normal, regenerating, metaplastic, and neoplastic liver. J Pathol 188:201-6; Schmelzer et al. 2006. The phenotypes of pluripotent human hepatic progenitors. Stem Cells 24:1852-8).

One million (1×10e6) CD34+HSC cells are co-transferred with 1×10e6 parenchyma cells (10e5 EpCAM+ hepatoblasts) into the liver of 1- to 3-day-old DKO or AFK8/DKO mice previously irradiated at 400 rad (sublethal). 20-30 DKO-hu mice are generated from each fetal liver tissue donor.

Human T/B/DC cells are analyzed by FACS at different time points after HSC transplant as previously reported (FIG. 1; Meissner et al. 2004. Characterization of a thymus-tropic HIV-1 isolate from a rapid progressor: role of the envelope. Virology 328:74-88; Su et al. 1995. HIV-1-induced thymocyte depletion is associated with indirect cytopathogenicity and infection of progenitor cells in vivo. Immunity 2:25-36). Human cells (CD45+) are analyzed for CD4, CD8, CD25 (Treg), HLA-DR (activated T cells), CD27/CD45RO (naïve and memory T cell subsets), CD19 (B cells), CD11c (mDC) and CD123 (PDC). Antibodies with appropriate labels are purchased from BD-Pharmingen.

When the parenchyma cell suspensions prepared from fetal livers were analyzed, 12% of liver cell suspensions from fetal livers are EpCAM+ cells, of which more than 80% are hepatoblasts and hepatic stem cells (Schmelzer et al. 2006. The phenotypes of pluripotent human hepatic progenitors. Stem Cells 24:1852-8). Thus, the parenchyma cells prepared from fetal livers are enriched with human hepatoblasts.

These cells are co-injected in the liver of newborn DKO mice. As shown above, human CD34+ HSC reconstituted the human blood system with a functional human immune system. Regarding the hepatocyte reconstitution, human liver stem/progenitor cells have been documented in both CD34+ cells (Dan et al. 2006. Isolation of multipotent progenitor cells from human fetal liver capable of differentiating into liver and mesenchymal lineages. Proc Natl Acad Sci USA 103:9912-7) and in hepatocyte-like parenchyma EpCAM+ cells (Schmelzer et al. 2006. The phenotypes of pluripotent human hepatic progenitors. Stem Cells 24:1852-8). These progenitor cells injected in the liver give rise to human hepatocytes in the chimeric mouse.

Figures 3A, 3B:
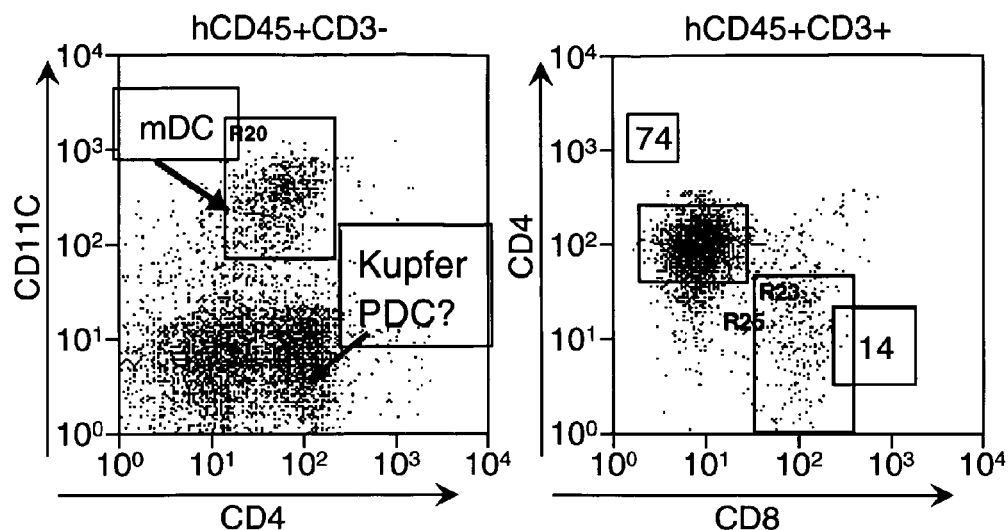
FIG. 3. Reconstitution of human leukocytes (CD45+) and hepatocytes (Alb+). (A-B): Both T cells and myeloid cells were present in the reconstituted liver. Leukocytes from DKO-hu HSC/Hep mice were isolated. A: human CD45+ CD3– cells were analyzed for CD4 and CD11c expression. All myeloid cell types (monocytes and macrophage/Kupfer cells; myeloid DC and PDC-CD123+, not shown) and B cells are present. B: human CD45+ CD3+ cells were analyzed for CD4 and CD8 expression. (C-E) Liver sections from DKO-hu HSC/Hep mice at 5 weeks post transplant were stained with anti-human albumin and DAPI. Human albumin+ cells are detected in the liver parenchyma (C) or around the central vein (D). E: no primary antibody control. Human Albumin+ cells exist in the liver parenchyma. All slides are counterstained with DAPI for DNA (blue). F: When the human albumin levels in the blood were measured in a representative cohort (n=7), a steady level of human albumin (150-350 ng/ml) was detected from 5-15 weeks post transplant. Pre-transplant sera were used as background (Non-tran).
Figures 3C, 3D, 3E:
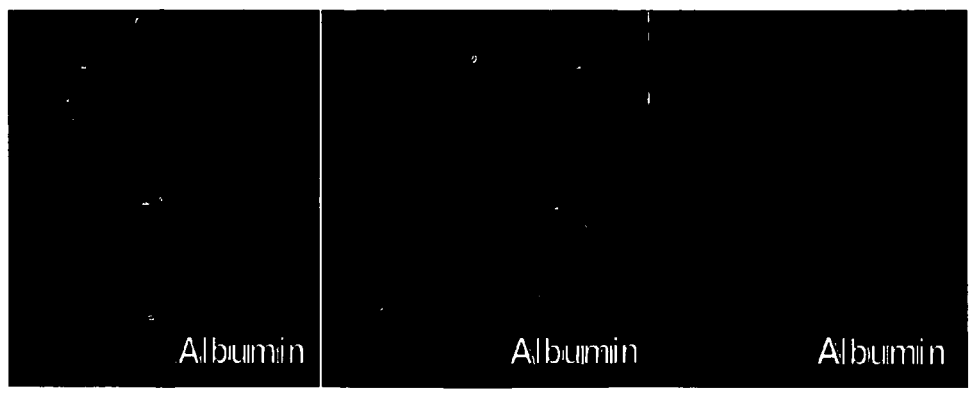
Figure 3F:
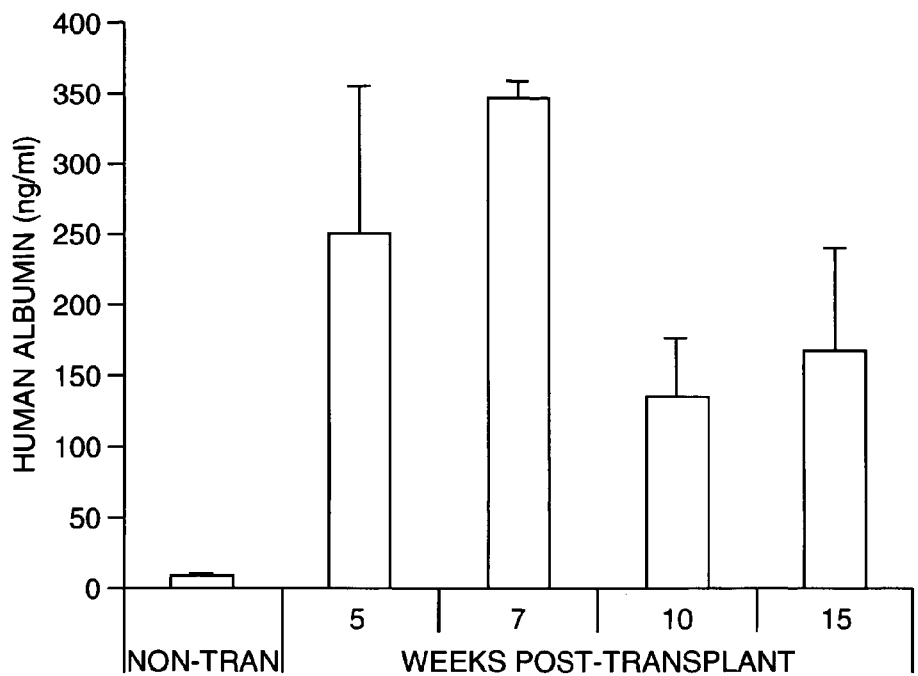

When CD34+ cells were co-transplanted with parenchyma hepatoblasts, significant and stable human albumin in the chimeric mouse blood was detected (FIG. 3). The engraftment of human blood cells was monitored by FACS for human leukocytes (>20% in total PBMC). Human albumin in the plasma of mice was measured (100-500 ng/ml) by ELISA assay (FIG. 3F) and, for human hepatocytes, by IF staining of human Alb+ cells in the liver (FIG. 3C-E).

Example 4

Multiple Types of Human cells are Developed in the Liver of DKO-hu HSC/Hep Mice

When liver leukocytes from the DKO-hu HSC mouse were isolated, 80% showed human CD45+ expression. Both lymphoid cells and myeloid cells were present in the reconstituted liver (FIG. 3A-B). Immuno-staining of liver section also demonstrates reconstitution of human hepatocytes (Albumin+, FIG. 3C-E). Therefore, human hepatocytes as well as human T/B/myeloid cells are present in the chimeric liver.

Example 5

FKBP-Casp8Transgenic Mice with Inducible death of Liver Cells

The DKO-hu HSC/Hep mouse model was improved by 1) boosting human hepatocyte cell growth with anti-human c-Met mAb, and 2) by selective ablation of murine hepatocytes (AFC8/DKO-hu HSC/Hep mice).

The newborn BalbC/Rag2$^{-/-}\gamma_c^{-/-}$ DKO mouse is currently the most permissive mouse model for the engraftment of human tissues, allowing long-term development of human primary and secondary immune organs. When human liver stem/progenitor cells (hepatoblasts) are transplanted into newborn (1-3 days) DKO mice, human liver cells are also detected in the chimeric mice. However, the levels of human hepatocyte engraftment is relatively low. Therefore, to enhance human liver cell engraftment in the DKO-hu mouse, murine hepatocyte death is induced after human liver cell transfer.

Figure 4A:
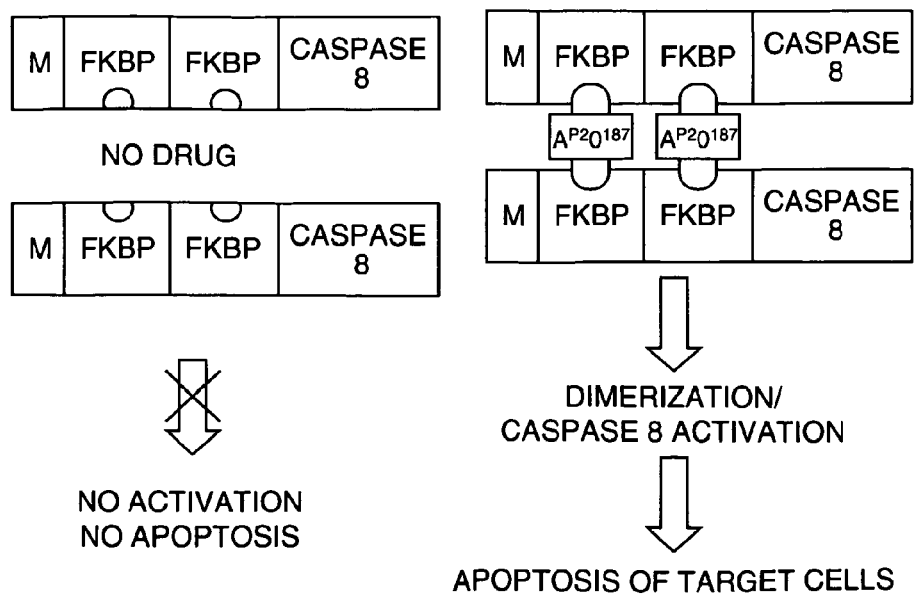
FIG. 4. Generation of the FKBP-Casp8 fusion gene with inducible cell killing activity. (A) Inducible activation of Caspase 8 through dimerization. The chemical dimerizer AP20187 causes dimerization/activation of Caspase 8 through interaction of adjacent FKBP binding sites. M, myristoylation signal; FKBP, FK506 binding domain; caspase, human activated caspase 8 (fragment Ser217-Aps479. ref) was cloned into the pC4M-Fv2E vector (Ariad Pharmaceuticals) to express the FKBP2-Casp8 fusion protein whose activation is induced by dimerization with AP20187. (B-C) Dose-dependent induction of apoptosis in cells transfected with FKBP-Caspase 8. 293T cells were co-transfected with plasmids expressing eGFP alone, or with CMV-promoter driven FKBP-Casp8. Transfected cells were cultured for 30 hours and then various amounts of AP20187 dimerizer was added. The cells were then cultured for 24 hours, harvested, stained with 7AAD, and analyzed by FACS for GFP and 7AAD. (B) GFP+ (transfected) cells were gated and the percentage of dead cells (7AAD+) was analyzed. (C) GFP– (untransfected bystander) cells were similarly analyzed. At least 3 independent experiments are repeated.
Figure 4B:
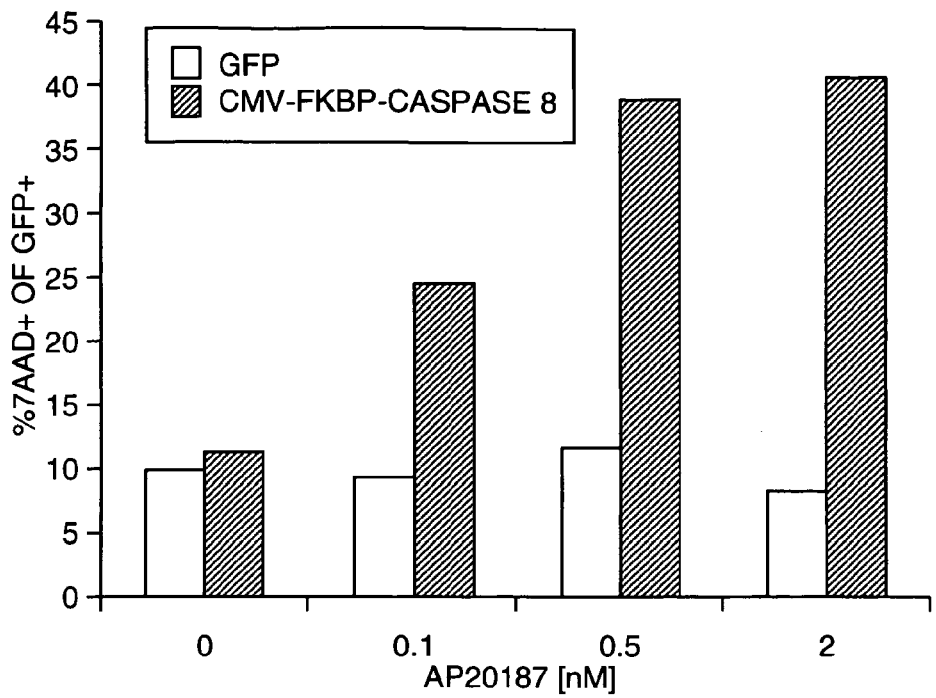
Figure 4C:
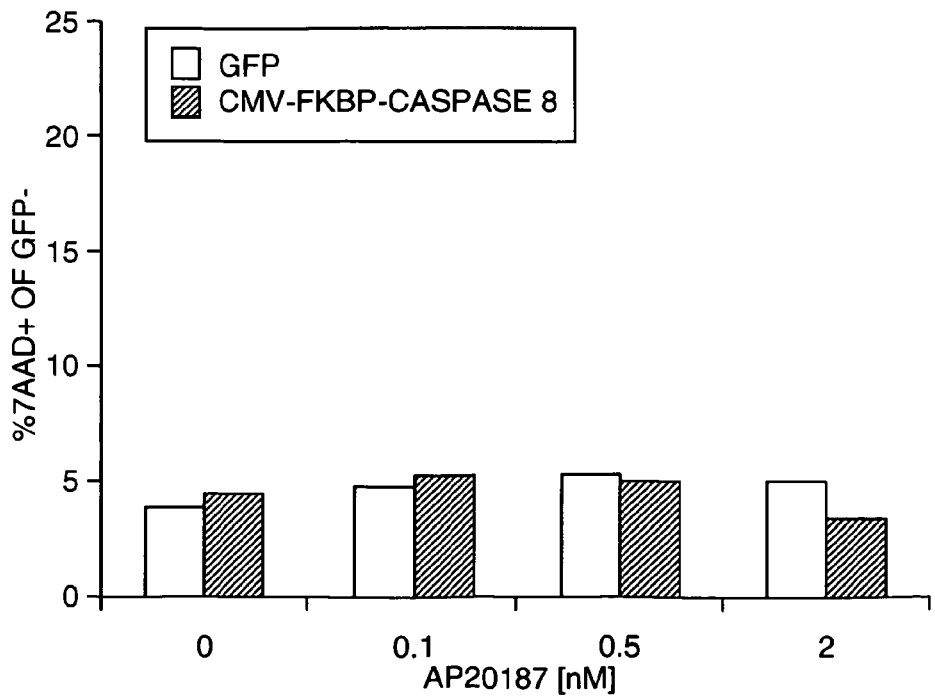

The FKBP-Caspase8 fusion gene with inducible cell killing activity was constructed (FIG. 4; and Chang et al. 2003. Activation of procaspases by FK506 binding protein-mediated oligomerization. Sci STKE 2003:PL1). Addition of FKBP dimerizer AP20187 to cells transfected with the FKBP-Casp8 and/or GFP led to death of GFP+/FKBP-Casp8+ cells, but not GFP− bystander cells, in a dose-dependent fashion (FIG. 4B/C). The drug had no detectable effect on cells transfected with only GFP expressing gene. Therefore, FKBP-Casp8 activation by AP20187 kills target cells expressing the gene but not bystander cells, an important point for depleting specific target cells in vivo.

DKO female mice are super-ovulated and fertilized eggs are isolated by standard procedures in the UNC transgenic core facility. The Alb-FKBP-Casp8 transgene is injected into fertilized DKO eggs and implanted into surrogate mother mice. Screening for the Alb-FKBP-Casp8 transgene is done with PCR (FIG. 5C; Kovalev et al. 2001. An important role of CDK inhibitor p18(INK4c) in modulating antigen receptor-mediated T cell proliferation. J Immunol 167:3285-92). FKBP-Casp8/DKO transgenic founders are confirmed by Southern blot and its expression confirmed by western/IF (anti-human Caspase 8 mAb) of liver tissues. Spleen, kidney, heart and thymus are used as control tissues. After establishing the AFC8/DKO founder mice that express the fusion protein in the liver, we test the dose and duration of AP20187 to induce hepatocyte apoptosis in the mouse. For peritoneal injections, AP20187 (Ariad Pharmaceuticals) is prepared (1 mg/ml in a solution consisting of 4% ethanol, 10% PEG-400, and 1.7% Tween). The AP20187 dose is adjusted to deliver 0.25, 1, 4 and 10 mg/kg (3-5 mice/dose). This dose range of AP20187 is effective in inducing Capsase8 activation and target cell depletion. No toxicity is observed in mice because AP20187 is engineered for in vivo purposes and does not interact with endogenous FKBP (Burnett et al. 2004. Conditional macrophage ablation in transgenic mice expressing a Fas-based suicide gene. J Leukoc Biol 75:612-23; Pajvani et al. 2005. Fat apoptosis through targeted activation of caspase 8: a new mouse model of inducible and reversible lipoatrophy. Nat Med 11:797-803).

The AFC8/DKO mouse was used to construct AFC8/DKO-hu HSC/Hep mice as described above. At 3-8 weeks post transplant of human cells, AP20187 is administered to induce death of murine hepatocytes. Hepatocyte depletion is monitored by measuring serum ALT level and increased human hepatocytes by blood levels of human albumin at 1, 2, 4, 6 and 8 weeks post drug treatment. At 2, 4 and 8 weeks post induction, we harvest the chimeric liver of selected AFC8/DKO-hu HSC/Hep mice to monitor murine hepatocyte death (apoptosis markers) and human hepatocytes (human albumin+ cells), and expression of other human liver-specific genes listed above.

For peritoneal injections, AP20187 (Ariad Pharmaceuticals) is prepared (1 mg/ml in a solution consisting of 4% ethanol, 10% PEG-400, and 1.7% Tween). The AP20187 dose is adjusted to deliver 0.25, 1, 4 and 10 mg/kg (3-5 mice/dose). This dose range of AP20187 is effective in inducing Capsase8 activation and target cell depletion. No toxicity is observed in mice because AP20187 is engineered for in vivo purposes and does not interact with endogenous FKBP (Burnett et al. 2004. Conditional macrophage ablation in transgenic mice expressing a Fas-based suicide gene. J Leukoc Biol 75:612-23; Pajvani et al. 2005. Fat apoptosis through targeted activation of caspase 8: a new mouse model of inducible and reversible lipoatrophy. Nat Med 11:797-803).

Figure 5A:
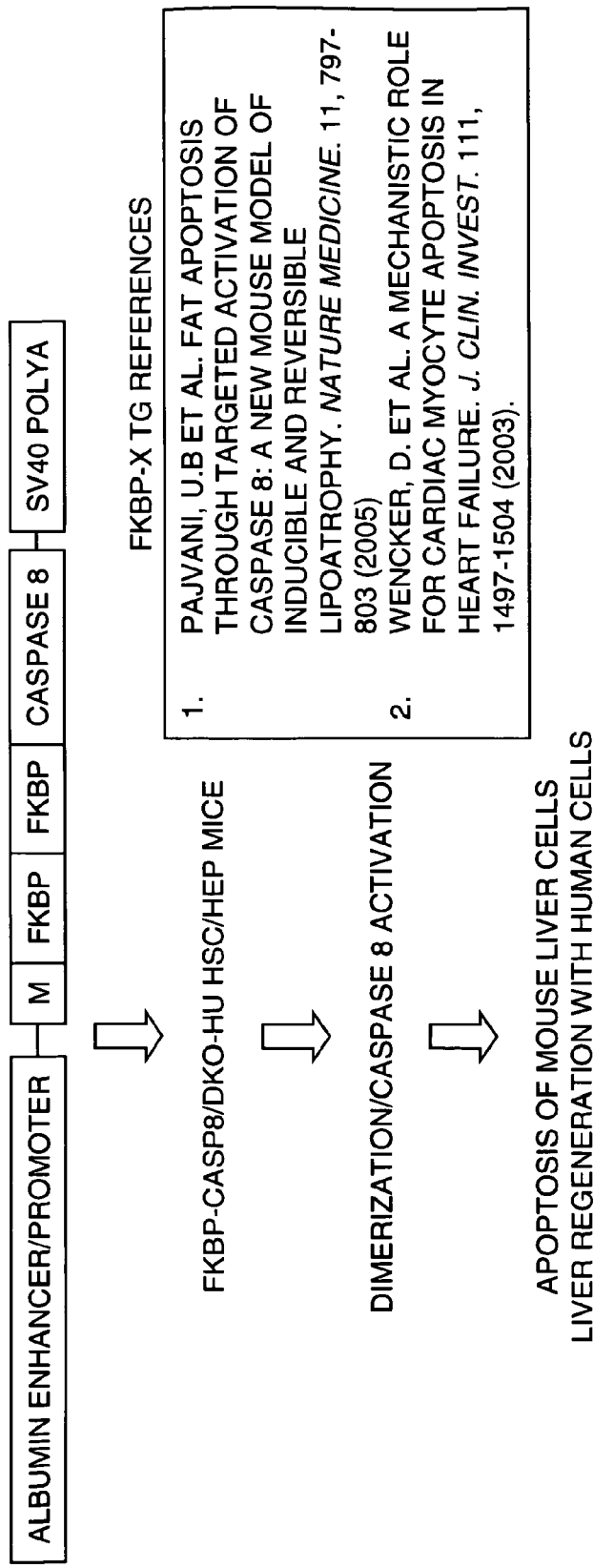
FIG. 5. Generation of Alb-FKBP-Casp8 transgenic DKO (AFC8/DKO) mice. (A) The Alb-FKBP-Casp8 transgene structure and AFC8/DKO-hu HSC/Hep mice: the FKBP2Casp8 fusion gene was cloned into the liver specific transgenic construct with the Albumin promoter (see Heckel et al. 1990. Neonatal bleeding in transgenic mice expressing urokinase-type plasminogen activator. Cell 62:447-56). (B) Hepatocyte-specific apoptosis with expression from the albumin promoter/enhancer. Alb-FKBP-Casp8 functions in HepG2 but not 293T cells. As described in FIG. 6B, the FKBP-Casp8 gene controlled by CMV enhancer or the hepatocyte-specific albumin promoter was co-transfected with GFP-expressing plasmid in 293T and HepG2 cells. Transfected cells were cultured for 30 hours and AP20187 dimerizer (2 nM) was added to the culture medium. The cells were then cultured for 24 hours, harvested, stained with 7AAD, and analyzed for GFP and 7AAD. GFP+ cells were analyzed for 7AAD uptake (dead cells). (C) Generation of Alb-FKBP-Casp8/DKO transgenic mice. Standard transgenic mouse procedure was used to inject the transgene construct into fertilized DKO embryos. In the initial screening of 11 mice from two injections, one transgenic founder was identified. PCR is run using primers that amplify the transgenic construct or the mouse endogenous p18 gene (see Kovalev et al. 2001. An important role of CDK inhibitor p18(INK4c) in modulating antigen receptor-mediated T cell proliferation. J Immunol 167:3285-92). 300 fg of transgene plasmid DNA, 100 ng of mouse genomic DNA, a mixture of 300 fg plasmid+ 100 ng mouse DNA, Water+PCR mixture, and DNA from a transgenic founder mouse was shown.
Figure 5B:
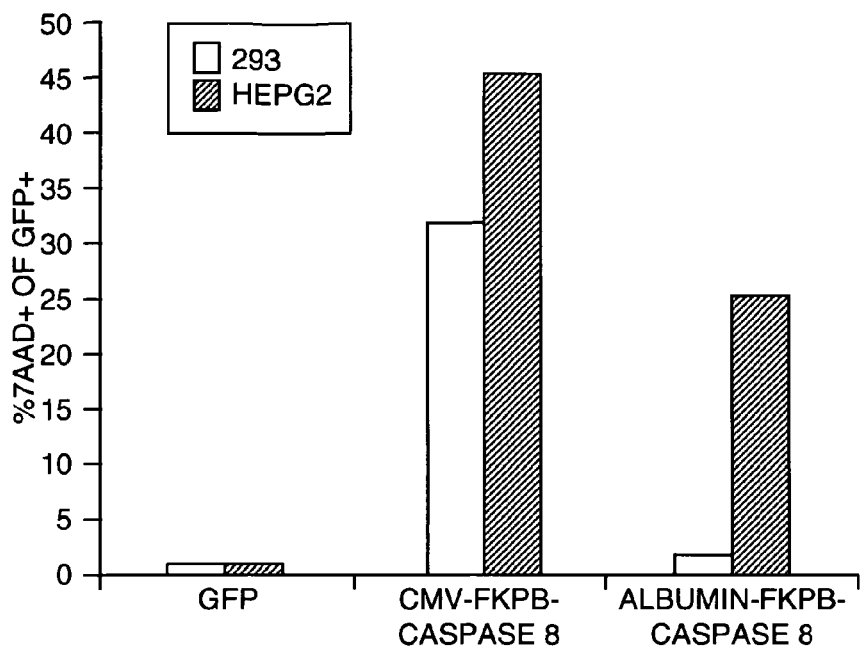
Figure 5C:
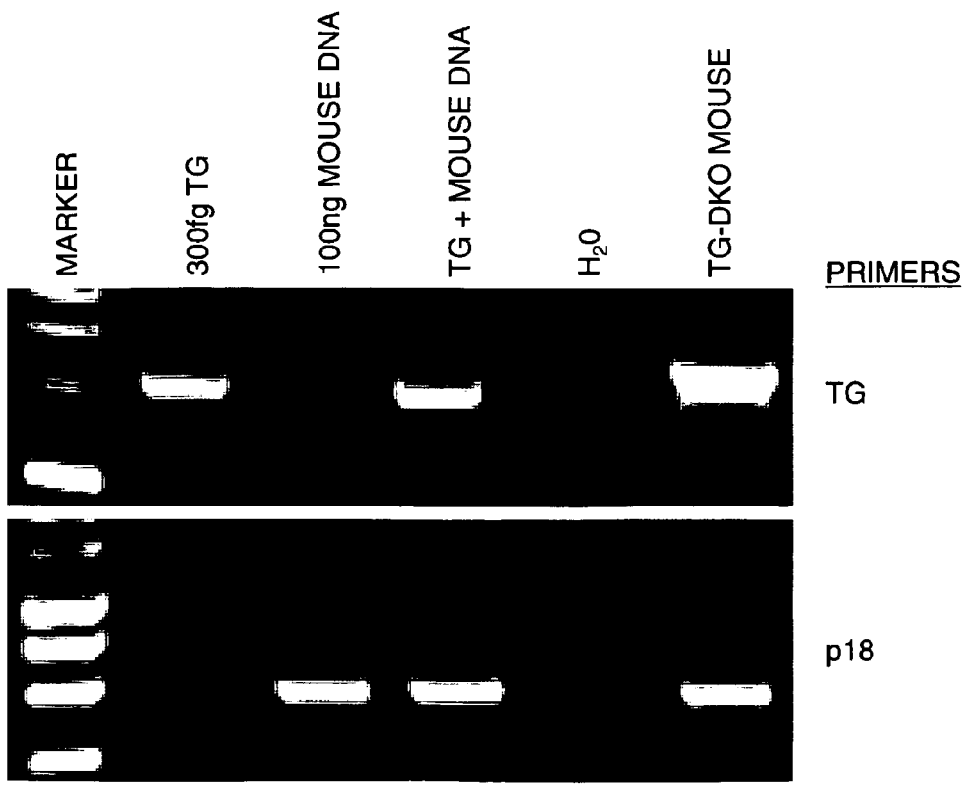

When expressed from the liver-specific albumin promoter in the transgenic construct (FIG. 5A; and Heckel et al. 1990. Neonatal bleeding in transgenic mice expressing urokinase-type plasminogen activator. Cell 62:447-56), FKBP-Casp8 only kills HepG2 cells, but not 293T cells, in a dimer-dependent fashion (FIG. 5B). This confirms the hepatocyte-specific expression of the transgene. DKO transgenic mice have been generated with the Alb-FKBP-Casp8 construct (FIG. 5C).

Human hepatocyte level and functions are closely monitored by measuring human albumin expression. Expression of human liver-specific marker genes including human albumin, α-fetoprotein (AFP, highly expressed in fetal liver but not adult liver), CytochromeP450/CYP3A4 and CYP1A2 are measured by TaqMan RT-PCR and by detecting protein expression by IF, as reported (Azuma et al. 2007. Robust expansion of human hepatocytes in Fah(−/−)/Rag2(−/−)/Il2rg(−/−) mice. Nat Biotechnol 25:903-10; Meuleman et al. 2005. Morphological and biochemical characterization of a human liver in a uPA-SCID mouse chimera. Hepatology 41:847-56).

Figure 9A:
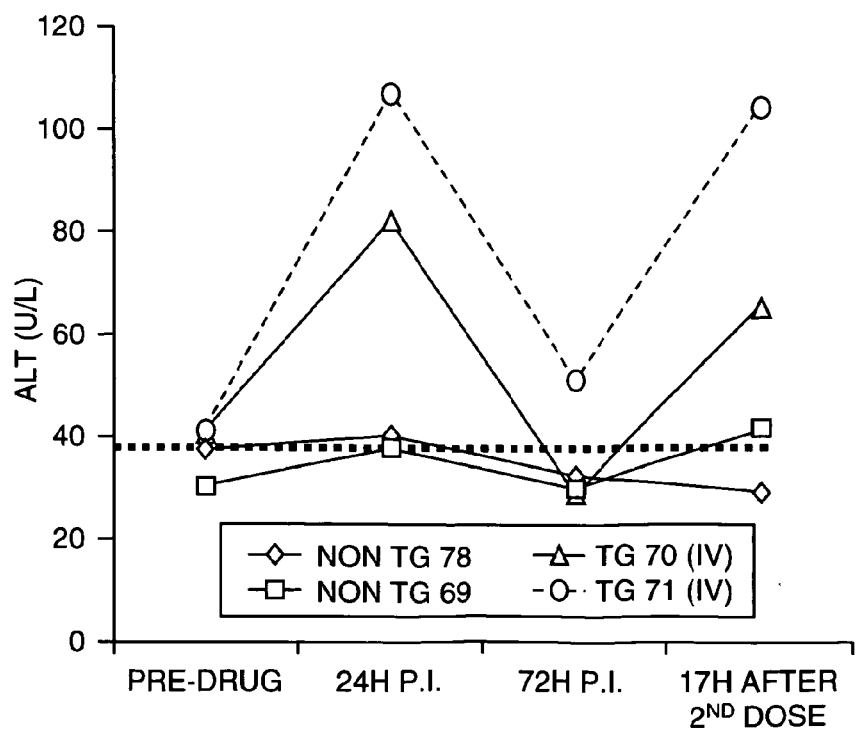
FIG. 9. Dimer injection in AFC8/DKO mice leads to transient mouse liver damage and enhanced human hepatocyte engraftment (50-100×). AFC8/DKO transgenic mice were treated with AP20187 (5 µg/g). A. Plasma ALT levels were measured at 24 hr and 72 hr (and 3-6 days, not shown) post treatment. A second injection of AP20187 6 days after 1st injection again leads to elevated ALT levels. Two non-TG DKO mice were used as controls (dashed line, background). B. Livers were harvested at 24 h after the 2nd injection and H&E stained. Accumulation of fat droplets (arrows) was observed in TG (but not in Non-TG) livers. V, vein. C. Enhanced human albumin levels in AP20187-treated AFC8-DKO-hu mice. AFC8/DKO or DKO mice were treated with AP20187 (5 µg/g) one hour prior to intra-splenic injection of human hepatocytes (2×10e6/mouse). Sera were collected at 80 days post transfer and human albumin levels were determined by ELISA. Thus, one injection of dimerizers significantly enhanced human hepatocyte engraftment (100×).
Figure 9B:
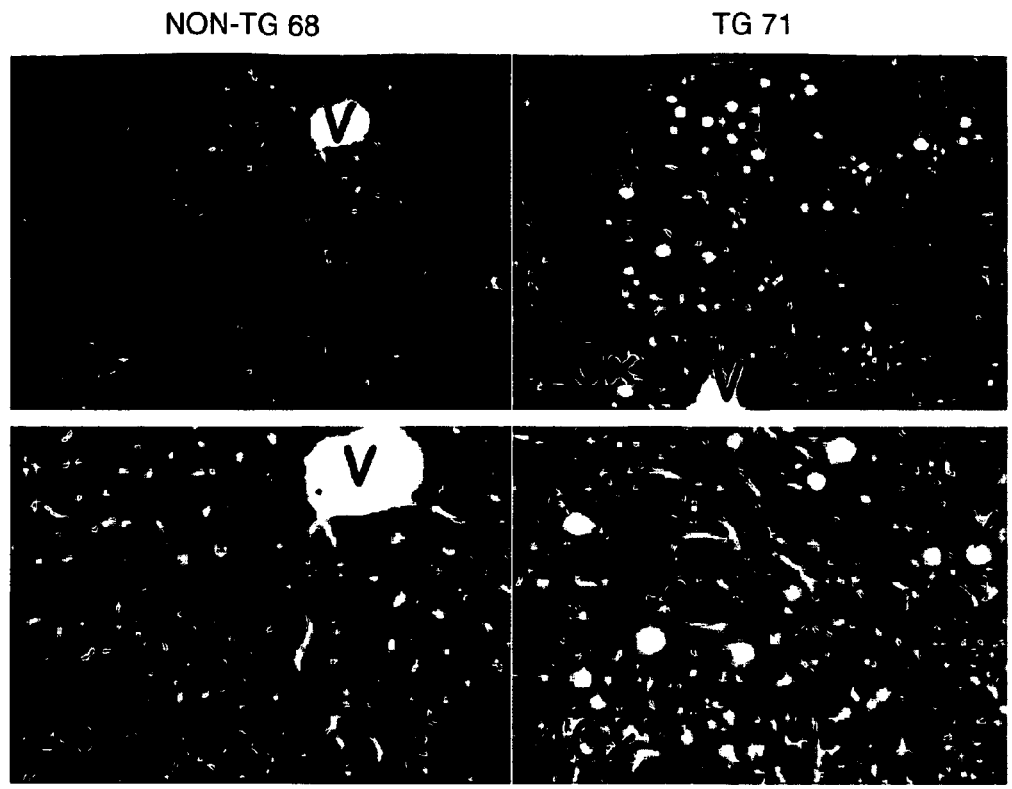
Figure 9C:
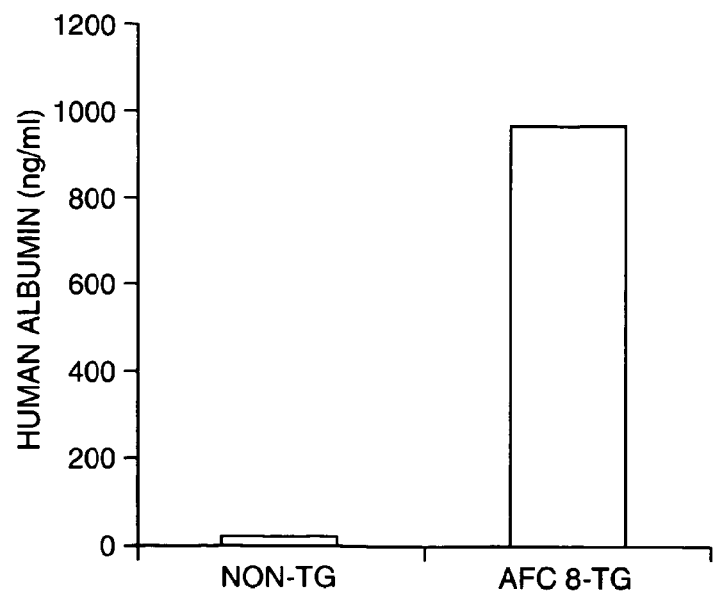

Dimer injection in AFC8/DKO mice led to transient mouse liver damage and enhanced human hepatocyte engraftment (50-100×) (FIG. 9). AFC8/DKO transgenic mice were treated with AP20187 (5 μg/g). Plasma ALT levels were measured at 24 hr and 72 hr (and 3-6 days, not shown) post treatment (FIG. 9A). A second injection of AP20187 6 days after 1st injection again led to elevated ALT levels. Two non-TG DKO mice were used as controls (dashed line, background). Livers were harvested at 24 h after the 2nd injection and H&E stained (FIG. 9B). Accumulation of fat droplets (arrows) was observed in TG (but not in Non-TG) livers. V, vein. Enhanced human albumin levels were found in AP20187-treated AFC8-DKO-hu mice (FIG. 9C). AFC8/DKO or DKO mice were treated with AP20187 (5 μg/g) one hour prior to intra-splenic injection of human hepatocytes (2×10e6/mouse). Sera were collected at 80 days post transfer and human albumin levels were determined by ELISA. Thus, one injection of dimerizers significantly enhanced human hepatocyte engraftment (100×).

The improved DKO-hu HSC/Hep mouse is used for HBV, HCV and/or HIV infection.

Example 6

Agonistic Antibody Against Human c-Met

Hepatocyte Growth Factor (HGF) binds to c-Met (the HGF receptor) and is essential in the development and regeneration of the liver. To improve human hepatocyte growth, an agonistic antibody against human c-Met is used (c-Met mAb, mouse IgG1) that activates human but not murine c-Met as reported (Ohashi et al. 2000. Sustained survival of human hepatocytes in mice: A model for in vivo infection with human hepatitis B and hepatitis delta viruses. Nat Med 6:327-31).

In each cohort, 50% of the DKO-HSC/Hep mice are injected i.v. with the anti-C-Met mAb 3D1 (Genentech, South San Francisco, Calif.), at 50 µg/mouse weekly from 2-8 weeks post transplant (Ohashi et al. 2000. Sustained survival of human hepatocytes in mice: A model for in vivo infection with human hepatitis B and hepatitis delta viruses. Nat Med 6:327-31). Mouse IgG1 is used for controls. Human albumin levels are measured weekly in blood before, during and after treatment, and human hepatocytes are measured by IF of liver sections. Proliferation of human hepatocytes (Alb+) is analyzed by Ki67 staining or by in vivo BrDU pulse labeling followed by FACS or IF (Kovalev et al. 2001. An important role of CDK inhibitor p18(INK4c) in modulating antigen receptor-mediated T cell proliferation. J Immunol 167:3285-92). 3-4 cohorts are tested to monitor the anti-c-Met effect on human hepatocyte engraftment.

Example 7

Production of Antigen-Specific Human IgG in DKO-hu HSC Mice

Figure 8:
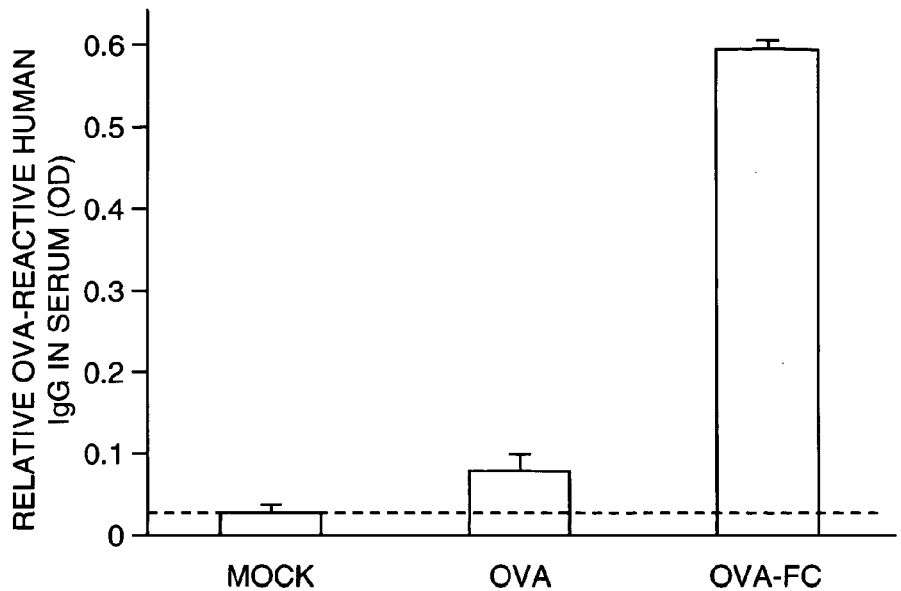
FIG. 8. Antigen-Fc fusion proteins give enhanced antigen-specific IgG induction in vivo.

Vaccination of the DKO-hu HSC mouse with a human HBV vaccine induced only IgM-producing human B cells but very low levels of human IgG+ B cells (FIG. 6). Human IgG+ B cells were increased by activating human T cells in the spleen in vitro with anti-CD3/CD28 mAb (FIG. 7). Similarly, immunization with the chicken ovalbumin protein induced very low levels of Ova-specific human IgG (FIG. 8). Ova-specific human IgG induction is enhanced by using the fusion protein between the same chicken ovalbumin protein with the Fc domain of human IgG (FIG. 8).

Example 8

HBV Infection of DKO-hu HSC/Hep Mice Leads to elevated Liver Inflammation and Long Term HBV Infection DKO-hu HSC/Hep mice were infected with HBV (patient serum, 1×10e9 HBV genomes/mouse) or mock. At 37 wpi, two mock and two HBV-infected mice were terminated.

Figure 10A:
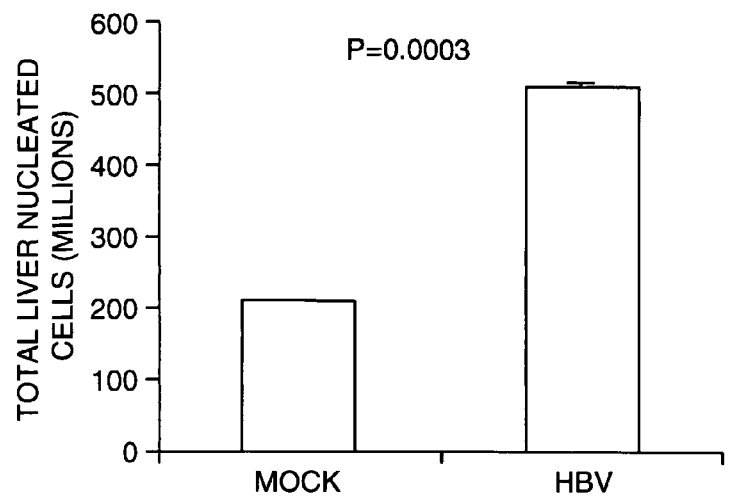
FIG. 10. HBV infection of DKO-hu HSC/Hep mice led to elevated liver inflammation and long term HBV infection. DKO-hu HSC/Hep mice were infected with HBV (patient serum, 1×10e9 HBV genomes/mouse) or mock. At 37 wpi, two mock and two HBV-infected mice were terminated. A. HBV-infected DKO-hu HSC/Hep mice had enlarged livers with 2-3× more nucleated cells. Error bars indicate SD and p value is shown. B. H&E staining of mock and HBV-infected livers. Elevated infiltration of leukocytes and vacuoles (arrows) were detected in the HBV-infected liver. C. HBV genome DNA in the infected mouse liver. Liver DNA (5 ng) was used to amplify HBV genome (core sequences) by nested PCR (HBV core sequences). 1. mock liver DNA; 2. HBV-infected liver DNA; 3. 3,000 HBV genomes+mock liver DNA; and 4. 300,000 HBV genomes+mock liver DNA. D. Detection of HBV+ cells with the Anti-HBV core antibody in the HBVinfected DKO-hu liver. Liver section from the infected mouse was stained with anti-HBV core antibody, and HBV+ cells are indicated by the arrows. Isotype controls or mock liver sections show no signals (not shown).
Figure 10B:
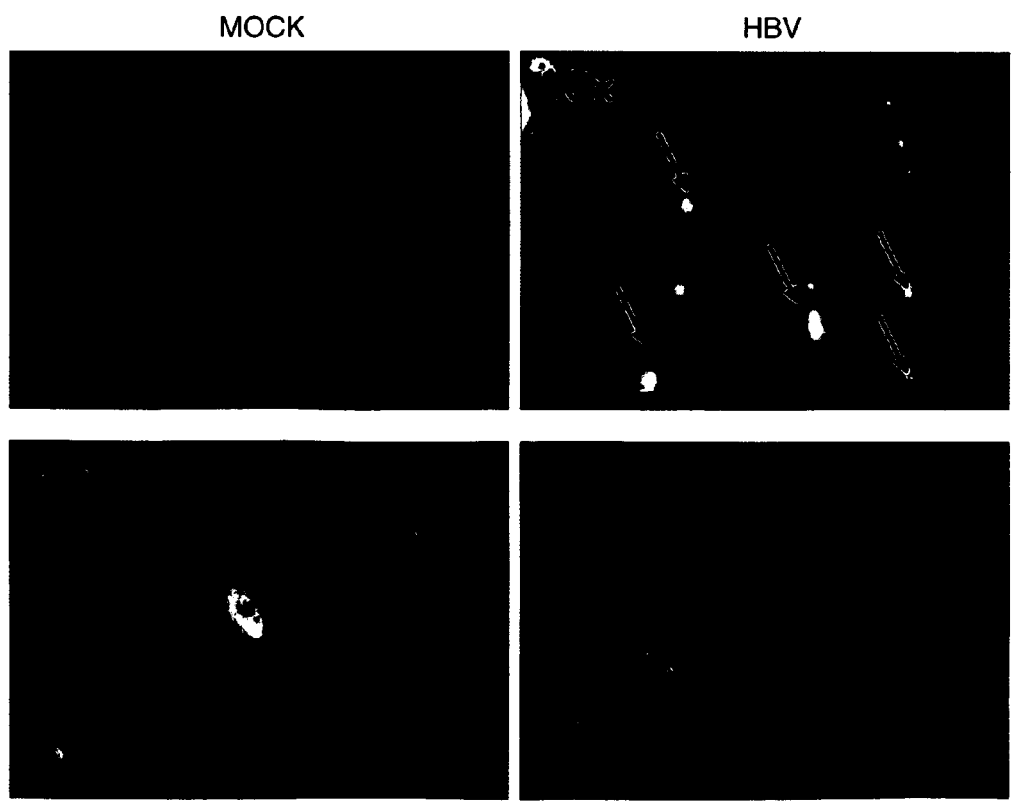
Figure 10C:
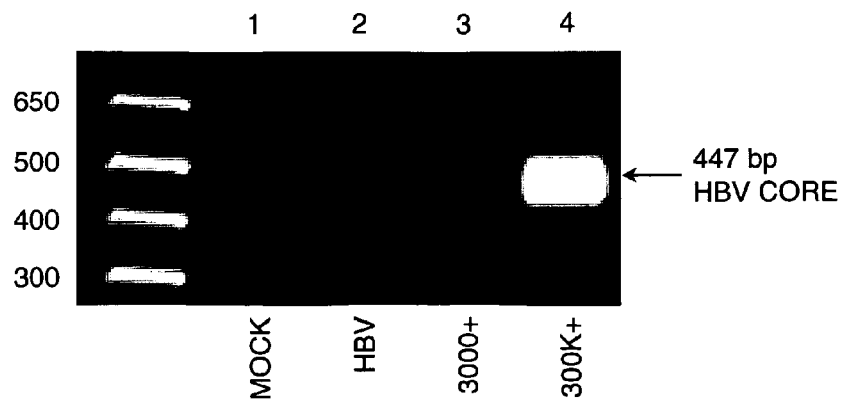
Figure 10D:
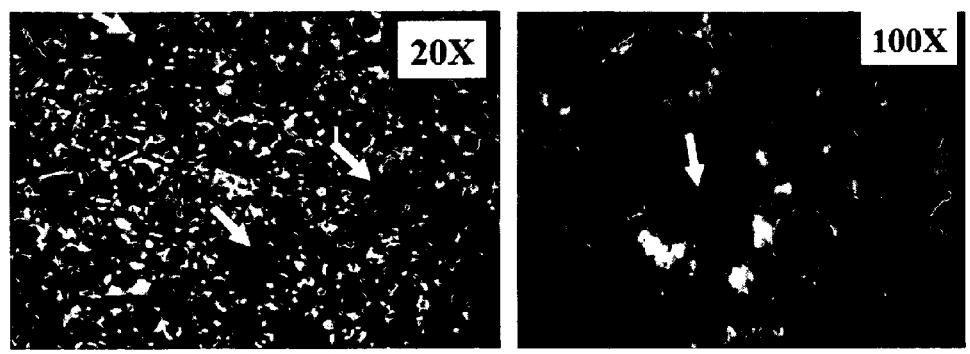

HBV-infected DKO-hu HSC/Hep mice had enlarged livers with 2-3× more nucleated cells (FIG. 10A), and elevated infiltration of leukocytes and vacuoles (arrows) were detected in the HBV-infected liver (FIG. 10B). The HBV genome DNA was detected in the infected mouse liver (FIG. 10C), and HBV+ cells were also detected with the Anti-HBV core antibody (FIG. 10D).

Example 9

HCV Infection in DKO-Hu HSC/Hep Mice is Associated with Elevated Levels of T Cell Activation and Liver Pathology DKO-hu HSC/Hep mice were infected with HCV (patient serum, 1×10e7 HCV genomes/mouse) or mock. At 25 wpi, two mock and one HCV-infected mice were analyzed. A. HCV genome RNA in the infected mouse blood was detected (2×10e5 copies/ml). Mock infected mice showed background level and patient HCV stock was also used as a control. B. HCV-infected DKO-hu HSC/Hep mice had higher levels of activated CD4 or CD8 T cells (% HLA-DR+). C. H&E and anti-human albumin staining of HCV-infected livers. Human albumin+hepatocytes and vacuoles were detected in the HCV-infected liver. HCV+ hepatocytes in the liver tissue are also measured.

Figure 11A:
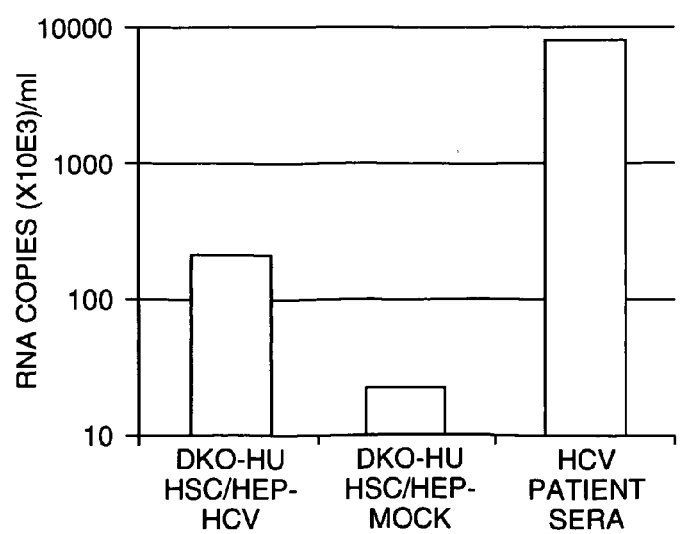
FIG. 11. HCV infection in DKO-hu HSC/Hep mice is associated with elevated levels of T cell activation and liver pathology. DKO-hu HSC/Hep mice were infected with HCV (patient serum, 1×10e7 HCV genomes/mouse) or mock. At 25 wpi, two mock and one HCV-infected mice were analyzed. A. HCV genome RNA in the infected mouse blood was detected (2×10e5 copies/ml). Mock infected mice showed background level and patient HCV stock was also used as a control. B. HCV-infected DKO-hu HSC/Hep mice had higher levels of activated CD4 or CD8 T cells (% HLA-DR+). C. H&E and anti-human albumin staining of HCV-infected livers. Human albumin+ hepatocytes and vacuoles were detected in the HCV-infected liver.
Figure 11B:
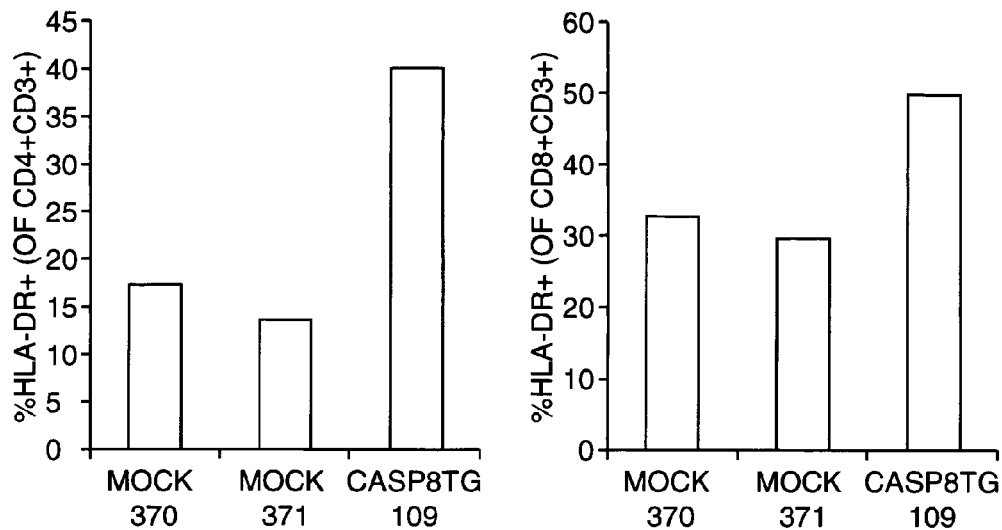
Figure 11C:
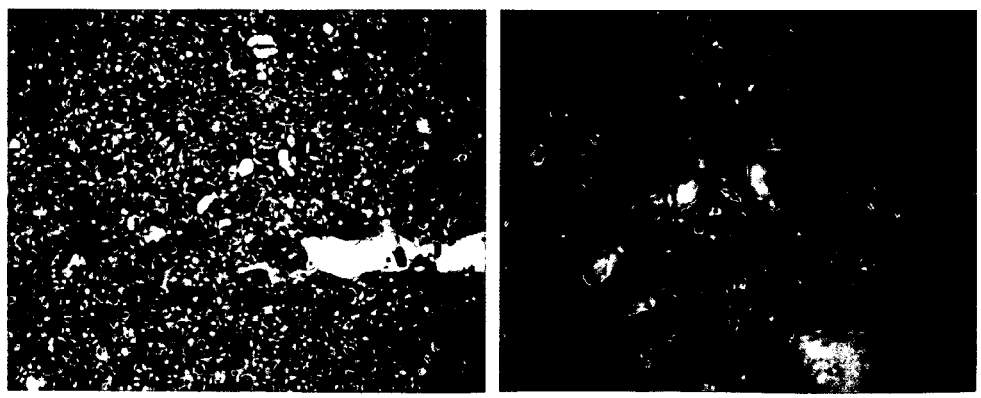

HCV genomes were detected in the infected DKO-hu mice at 25 wpi, but not in mock infected DKO-hu mice or HCV-infected DKO mice (FIG. 11A and data not shown). In addition, elevated levels of activated human T cells were detected (FIG. 11B), as well as liver pathology characteristic of virus-induced hepatitis/liver diseases (FIG. 11C).

That which is claimed is:

1. A BalbC/Rag2$^{-/-}\gamma_c^{-/-}$ knockout transgenic mouse whose genome comprises a polynucleotide encoding a polypeptide having inducible toxicity to mouse liver cells, wherein the polypeptide comprises an FK506 binding domain (FKBP)-Caspase 8 fusion protein, and wherein the polynucleotide is operably linked to a liver-specific albumin promoter such that the polypeptide is expressed in liver cells of the transgenic mouse,
    said mouse further comprising:
    (a) an immune system comprising: human T cells, human B cells, human natural killer cells, human monocytes and macrophages and human dendritic cells, so that said mouse expresses a human immune system phenotype; and
    (b) a liver comprising human hepatocytes, so that said mouse expresses a human liver phenotype, wherein said human liver cells comprise at least 10% by volume of said liver of said mouse and the mouse maintains a steady level of human albumin from 5-15 weeks post transplant.

2. The mouse of claim 1, wherein said mouse is further infected with a Human immunodeficiency virus-1 (HIV-1), virus, a hepatitis virus, or both.

3. The mouse of claim 1, wherein said mouse is further infected with a hepatitis virus.

4. The mouse of claim 3, wherein said hepatitis virus is Hepatitis B virus (HBV) or Hepatitis C virus (HCV).

5. A method of making a transgenic mouse comprising an immune system, said immune system comprising: human T cells, human B cells, human natural killer cells, human monocytes and macrophages and human dendritic cells, so that said mouse expresses a human immune system phenotype; and a liver comprising human hepatocytes, so that said mouse expresses a human liver phenotype;
    said method comprising the steps of:
    (a) providing a BalbC/Rag2$^{-/-}\gamma_c^{-/-}$ knockout transgenic mouse whose genome comprises a polynucleotide encoding a polypeptide having inducible toxicity to mouse liver cells, wherein the polypeptide comprises an FK506 binding domain (FKBP)-Caspase 8 fusion protein, and wherein the polynucleotide is operably linked to a liver-specific albumin promoter such that the polypeptide is expressed in liver cells of the transgenic mouse;

(b) transplanting human CD34+ hematopoietic stem cells into said transgenic mouse, wherein said stem cells differentiate into human T cells, human B cells, human natural killer cells, human monocytes and macrophages and human dendritic cells in said transgenic mouse;

(c) transplanting human liver progenitor cells into said transgenic mouse, wherein said human CD34+ hematopoietic stem cells and said human liver cells are autogeneic with respect to each other, and wherein said human liver progenitor cells form human hepatocytes in said liver of said transgenic mouse; and then, (d) inducing said toxicity in the transgenic mouse cells to thereby selectively kill the mouse liver cells, wherein said human hepatocytes comprise at least 10% by volume of said liver of said mouse and the mouse maintains a steady level of human albumin from 5-15 weeks post transplant.

6. The method of claim 5, wherein said human liver cells comprise human parenchyma hepatoblasts.

7. The method of claim 5, wherein said human CD34+ hematopoietic stem cells and said human liver cells are transplanted simultaneously.

8. The method of claim 5, wherein said transplanting steps are carried out when said transgenic mouse is from 1 to 10 days old.

9. The method of claim 5, wherein said transplanting steps are carried out when said transgenic mouse is from 1 to 7 days old.

* * * * *

UNITED STATES PATENT AND TRADEMARK OFFICE
CERTIFICATE OF CORRECTION

PATENT NO.       : 9,173,383 B2
APPLICATION NO.  : 12/918676
DATED            : November 3, 2015
INVENTOR(S)      : Su et al.

Page 1 of 1

It is certified that error appears in the above-identified patent and that said Letters Patent is hereby corrected as shown below:

In the Claims:
Column 20, Claim 2, Lines 48 and 49:
　　Please correct "(HIV-1), virus, a hepatitis virus,"
　　　　to read -- (HIV-1) virus, a hepatitis virus, --

Signed and Sealed this
Twelfth Day of July, 2016

Michelle K. Lee
*Director of the United States Patent and Trademark Office*